US012748115B2

(12) United States Patent
Mizumura et al.

(10) Patent No.: US 12,748,115 B2
(45) Date of Patent: Sep. 29, 2026

(54) METHOD FOR PRODUCING AN EXDOTOXIN MEASURING AGENT

(71) Applicant: SEIKAGAKU CORPORATION, Tokyo (JP)

(72) Inventors: Hikaru Mizumura, Tokyo (JP); Maki Aizawa, Tokyo (JP); Toshio Oda, Tokyo (JP)

(73) Assignee: Seikagaku Corporation, Tokyo (JP)

( * ) Notice: Subject to any disclaimer, the term of this patent is extended or adjusted under 35 U.S.C. 154(b) by 1177 days.

(21) Appl. No.: 17/449,736

(22) Filed: Oct. 1, 2021

(65) Prior Publication Data

US 2022/0018841 A1 Jan. 20, 2022

Related U.S. Application Data

(63) Continuation of application No. 15/984,288, filed on May 18, 2018, now Pat. No. 11,162,949, which is a continuation of application No. 15/359,058, filed on Nov. 22, 2016, now abandoned, which is a continuation of application No. 14/704,230, filed on May 5, 2015, now abandoned, which is a continuation of application No. 14/001,138, filed as application No. PCT/JP2012/055728 on Feb. 28, 2012, now abandoned.

(60) Provisional application No. 61/447,556, filed on Feb. 28, 2011.

(51) Int. Cl.

*G01N 33/579* (2006.01)
*C12Q 1/34* (2006.01)
*C12Q 1/37* (2006.01)

(52) U.S. Cl.

CPC ............ *G01N 33/579* (2013.01); *C12Q 1/34* (2013.01); *C12Q 1/37* (2013.01); *G01N 2333/195* (2013.01); *G01N 2333/43508* (2013.01); *G01N 2333/96411* (2013.01); *G01N 2400/50* (2013.01)

(58) Field of Classification Search

CPC ........... G01N 33/579; G01N 2333/195; G01N 2333/43508; G01N 2400/50

See application file for complete search history.

(56) References Cited

U.S. PATENT DOCUMENTS

| | | | | |
|---|---|---|---|---|
| 5,550,030 | A | 8/1996 | Tanaka et al. | |
| 5,985,590 | A * | 11/1999 | Ding | C12Y 304/21084 435/7.1 |
| 6,849,426 | B2 | 2/2005 | Chen et al. | |
| 2009/0208995 | A1 | 8/2009 | Tamura et al. | |

FOREIGN PATENT DOCUMENTS

| | | | |
|---|---|---|---|
| CN | 105866080 | A * | 8/2016 |
| EP | 0291856 | A2 | 11/1988 |
| EP | 2050820 | A1 | 4/2009 |
| JP | 2011-244760 | A1 | 12/2011 |
| WO | WO 99/15676 | A2 | 4/1999 |
| WO | WO 03/002976 | A2 | 1/2003 |
| WO | WO 2008/004674 | A1 | 10/2008 |

OTHER PUBLICATIONS

Schneider et al. Sf9 cells: A versatile model system to investigate the pharmacological properties of G protein-coupled receptors. Pharmacology & Therapeutics 128 (2010) 387-418. (Year: 2010).*
Machine translation of CN105866080A (Year: 2016).*
Kwan et al., Hemolymph quality as indicator of health status in juvenile Chinese horseshoe crab *Tachypleus tridentatus* (Xiphosura) under laboratory culture, Journal of Experimental Marine Biology and Ecology, vol. 457, 2014, pp. 135-142. (Year: 2014).*
Martinho et al., Comparison of Endotoxin Levels in Previous Studies on Primary Endodontic Infections, Journal of Endodontics vol. 37, Issue 2, Feb. 2011, pp. 163-167. Published Jan. 14, 2011. (Year: 2011).*
Thorne et al., Evaluation of the Limulus Amebocyte Lysate and Recombinant Factor C Assays for Assessment of Airborne Endotoxin, Applied and Environmental Microbiology, vol. 76, No. 15, Aug. 2010, p. 4988-4995. Published Jun. 4, 2010. (Year: 2010).*
Dawson, Michael E., Ph.D., Harmonization of Endotoxin Standards and Units. LAL Update, vol. 15, No. 4, Dec. 1997, pp. 1-4. (Year: 1997).*
Alignment Figure of Amino Acid Sequences (created by GENETYX) of Tachypleus tridentatus Factor C and Carcinoscorpius rotundicauda Factor C, Nov. 14, 2016.
Decision of Refusal received in Japanese Patent Application No. 2013-538748 dated Dec. 13, 2017.
Ding, et al., Expression of Full Length and Deletion Homologues of Carcinoscorpius rotundicauda Factor C in *Saccharomyces cerevisiae*: Immunoreactivity and Endotoxin Binding, Journal of Endotoxin Research 4(1):33-43, 1997.
GenBank: S77063.1. Amino Acid Sequence of CrFC21 (factor C from Carcinoscorpius rotandicauuda), 1995.
Hideki Yamaji, SCEJ, 42nd Autumn Meeting, 2010, p. 673.
Hom and Volkman, BioTechniques, vol. 25, 1998, pp. 18-20.
Iwanaga, The Limulus Clotting Reaction, Current Opinion in Immunology 5:74-82, 1993.
Invitrogen p, ZV5vector kit, 2008, 44 pages.
Kathy Hancok, et al., Journal of Immunological Methods, vol. 330, 2008, pp. 130-136.

(Continued)

*Primary Examiner* — Laura Schuberg
*Assistant Examiner* — Nicholas A Humphries
(74) *Attorney, Agent, or Firm* — Knobbe, Martens, Olson & Bear, LLP

(57) ABSTRACT

A method for rapidly and highly sensitively measuring endotoxin relies on an endotoxin-measuring agent, which includes a factor C derived from *Tachypleus tridentatus* that does not have His-tag sequence at the C-terminus, a factor B of a horseshoe crab, and a proclotting enzyme of a horseshoe crab. Each of these proteins can be a recombinant protein obtainable by being expressed using a stably expressing cell line of an insect cell as a host.

8 Claims, 9 Drawing Sheets

Specification includes a Sequence Listing.

(56) References Cited

OTHER PUBLICATIONS

L. Ikonomou, et al., Appl Microbiol Biotechnol, vol. 62, 2003, pp. 1-20.
Maeda, et al., Effects of His-tag on the Molecular Surf Ace Functionalities of Cystatin C, Proceedings of Symposium of the Japan Society for Bioscience, Biotechnology, and Agrochemistry, p. 278, 3B01a11, 2008.
Maekawa, Mass Production of Proteins Using Baculovirus—Insect Cell Expression System, Protein Science Society of Japan, Archives e022, vol. 1, 2008.
Mason, et al., Differential Effect of a His Tag at the N- and C-Termini: Functional Studies with Recombinant Human Serum Transferrin, Biochemistry 41:9448-9454, 2002.
Morais, V.A., Expression and Characterization of Recombinant human α-3/4-fucosyltransferase III From Spodoptera frugiperda (Sf9) and Trichoplusia ni (Tn) Cells Using the Baculovirus Expression System, Biochem J. 353:719-725, 2001.
Muta et al., Limulus factor C. An Endotoxin-Sensitive Serine Protease Zymogen With a Mosaic Structure of Complement-Like, Epidermal Growth Factor-Like, and Lectin-Like Domains, The Journal of Biological Chemistry 266(10):6554-6561, 1991.
Muta, T., et al., Horseshoe Crab Coagulation Factor B: A Unique Serine protease Zymogen Activated by Cleavage of an IIe-IIe Bond, The Journal of Biological Chemistry 268(28):21384-21388, 1993.
Nakamura, et al., Lipopolysaccharide-Sensitive Serine-Protease Zymogen (Factor C) Found in Limulus Hemocytes, European Journal of Biochemistry 154:511-521, 1986.
Nakamura, et al., Purification and Properties of Intracellular Clotting Factor, Factor B, from Horseshoe Crab (*Tachypleus tridentatus*) Hemocytes, The Journal of Biochemistry 99(3):847-857, 1986.
Notification of Reasons for Refusal issued in corresponding Japanese Patent Application No. 2013-538748 dated Aug. 23, 2016.
Notification of Reasons for Refusal for corresponding Japanese Patent Application No. 2013-538748 dated Mar. 14, 2017.
Novagen Molecular Biology Catalog 2009/2010, Merck Ltd., Japan, 2009, Insect Cell Expression Vector Selection Guide, p. 134.
Office Action issued in corresponding European Patent Application No. 12 710 808.2 dated Jun. 24, 2014.
Office Action issued in corresponding Chinese Patent Application No. 201280010708.4 dated Sep. 19, 2014.
Office Action issued in corresponding Chinese Patent Application No. 201280010708.4 dated May 5, 2015.
Office Action issued in corresponding Japanese Patent Application No. 2013-538748 dated Jan. 5, 2016.
Office Action in Chinese Patent Application No. 201610799888. 9, dated Sep. 17, 2019.
Opposition to a Patent filed towards the corresponding Japanese patent No. 6640267 on Aug. 4, 2020.
Pui, et al., Yeast Recombinant Factor C From Horseshoe Crab Binds Endotoxin and Causes Bacteriostasis, Journal of Endotoxin Research 4(6):391-400, 1997.
Ramage, P., et al., Snags With Tags: Some Observations Made With (His)6-Tagged Proteins, Life Science ews (Japan Ed.) 4, 2002.
Search Report and Written Opinion issued in corresponding International Patent Application No. PCT/JP2012/055728 dated May 11, 2012.
Service Information of Comprehensive and Quantitative Profiling of Biological Samples-Derived Sugar Chain, Sugar Chain Analysis Using Mass Spectrometry by Medicinal Chemistry Pharmaceutical Co., Ltd., Nov. 10, 2016, URL: [https://www.funakoshi.co.jp/contents/8053].
Service Information of Contract Analysis Service by Sumitomo Bakelite Co., Ltd., Nov. 10, 2016, URL: [http://www.sumibe.co.jp/product/s-bio/glycan/contract/].
Service Information of Sugar Chain Analysis Service by COSMO BIO Co., Ltd., Nov. 8, 2016, URL: [http://www.cosmobio.co.jp/product/detail/lud_20101019.asp?entry_id=6586].
Third-party Observation issued in corresponding Japanese Patent Application No. 2013-538748 dated May 27, 2016.
Third-Party Observation filed in corresponding Japanese Patent Application No. 2018-074569 dated Jul. 23, 2019.
Vassilis Douris, et al., Advances in Virus Research, vol. 68, 2006, pp. 113-156.
Vector Map of pFastBac™1, multi-cloning site, Invitrogen Life Technologies, publication date unknown.
Wang, et al., Functional Expression of Full Length Limulus Factor C in Stably Transformed Sf9 cells, Biotechnology Letters 23:71-76, 2001.
Wang, et al., Closing and Expression of Tachypleus Tridentatus Factor C, Acta Biochimica et Biophysica Sinica 34(1):77-82, 2002.
Wu, W.-T., et al., Biopharmaceutical Technology, 2013.
Yuko Kawaguchi, et al., Journal of the Japanese Medical Association, 2012, vol. 8, No. 1, pp. 26-30.
European Examination Report for EP Application No. 19160846.2, dated Mar. 26, 2025 (in 5 pages).
Licari P. et al., “Modeling the population dynamics of Baculovirus-infected insect cells: Optimizing infection strategies for enhanced recombinant protein yields” Biotechnology and Bioengineering, vol. 39, No. 4, pp. 432-441, Feb. 20, 1992.
Murhammer, David W., in *Baculovirus and Insect Cell Expression Protocols*, “Transforming Lepidopteran insect cells for continuous recombinant protein expression” Humana Press, Dec. 31, 2007, Chapter 15 (pp. 299-315) and “Introduction to the use of Baculoviruses as biological insecticides” Chapter 18 (pp. 359-366).
USP chapter <85> Bacterial Endotoxins Test, Oct. 14, 2011, https://www.usp.org/sites/default/files/usp/document/harmonization/gen-method/q06_current_webpage_stage_6_monograph_23_nov_2011.pdf, 5 pages.

* cited by examiner

[Fig.1]
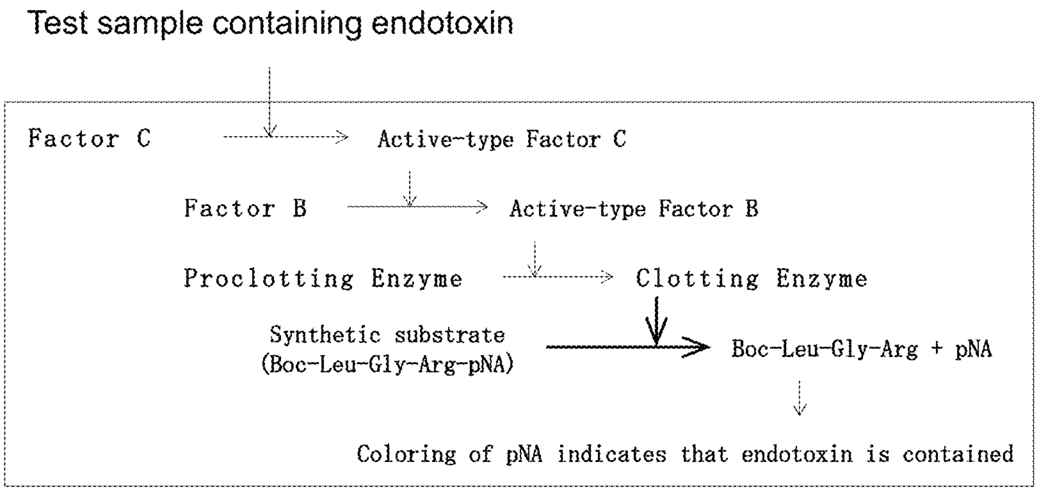

[Fig.2]
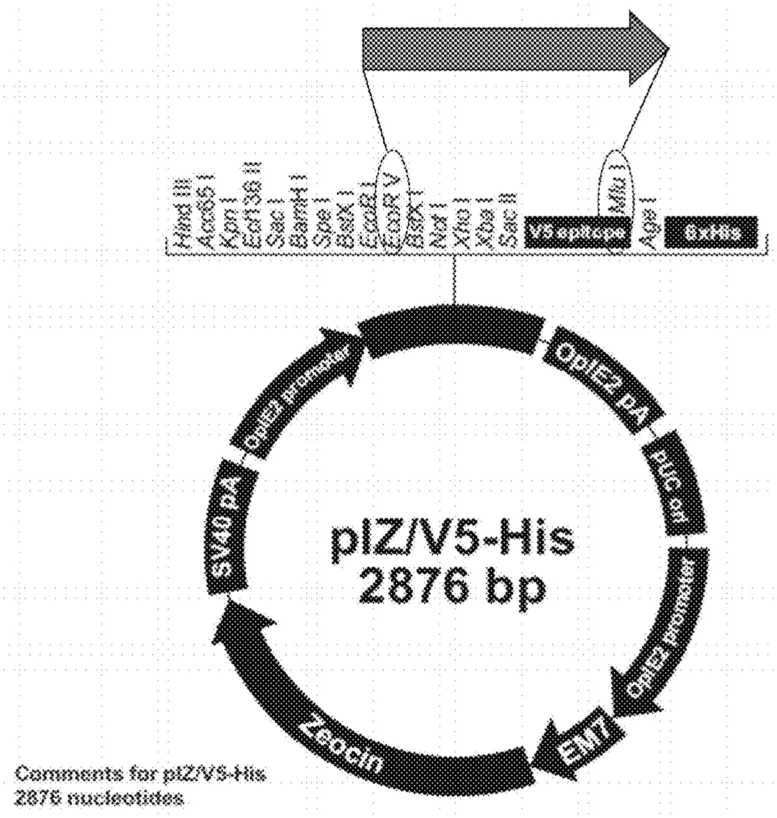

[Fig.3]
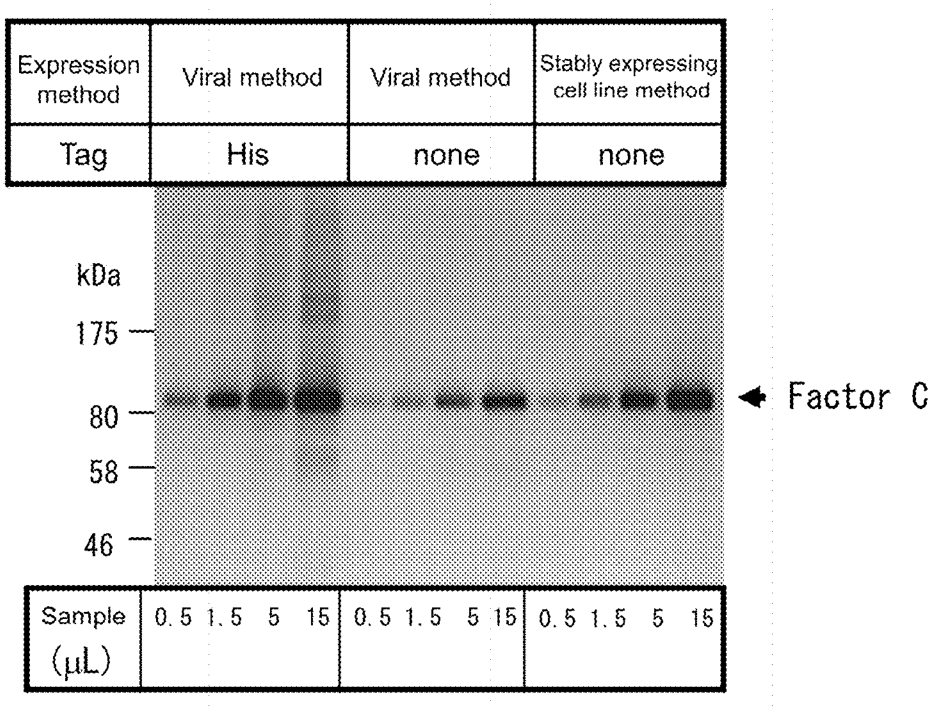
[Fig.4]
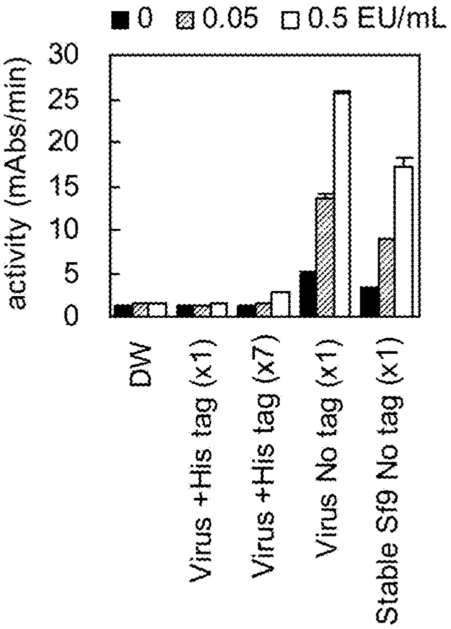

[Fig.5]
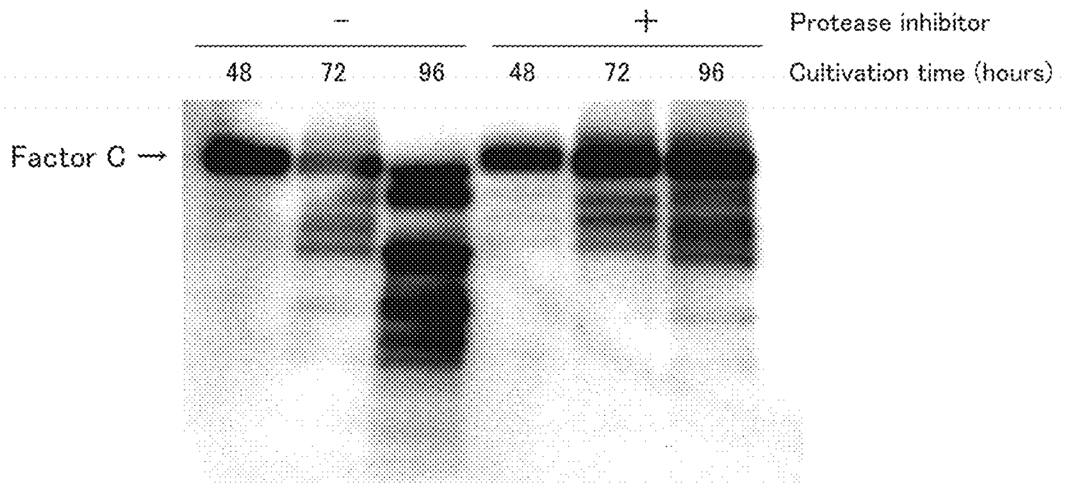

[Fig.6]
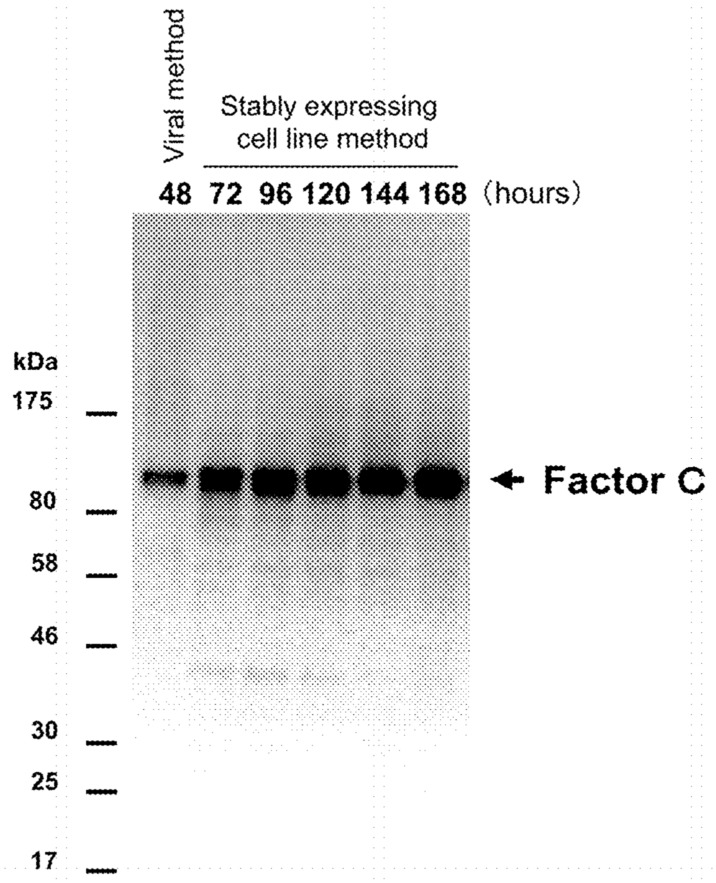

[Fig.7]
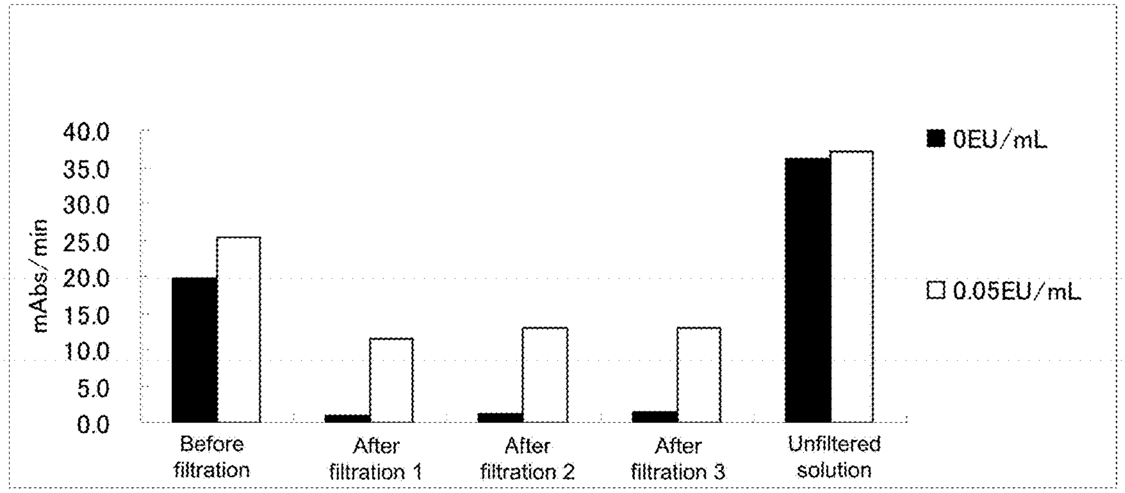
[Fig.8]
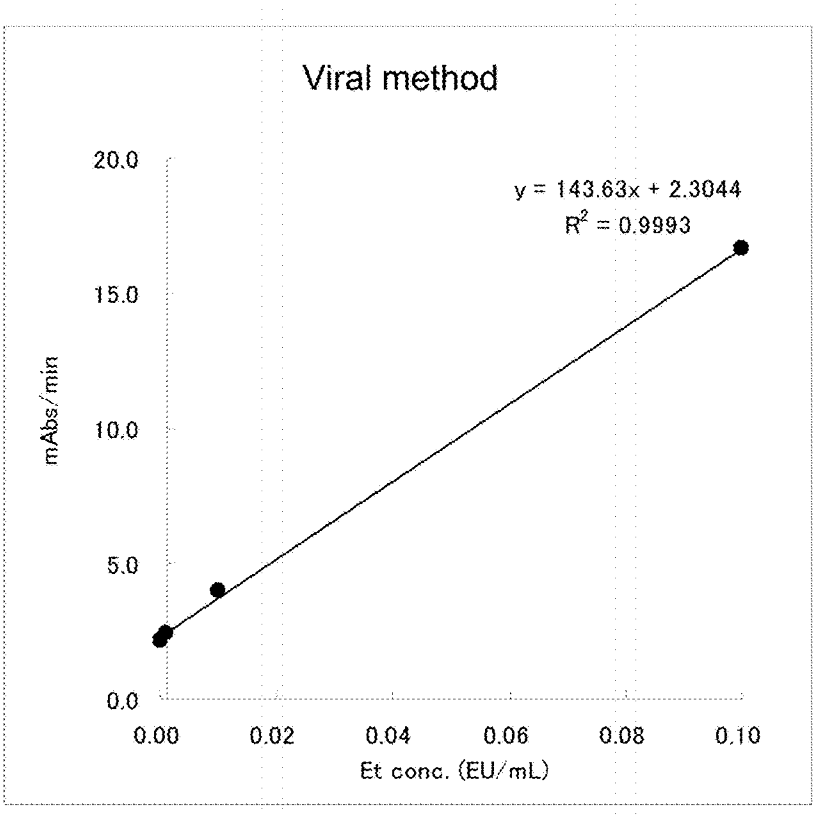

[Fig.9]
(a)
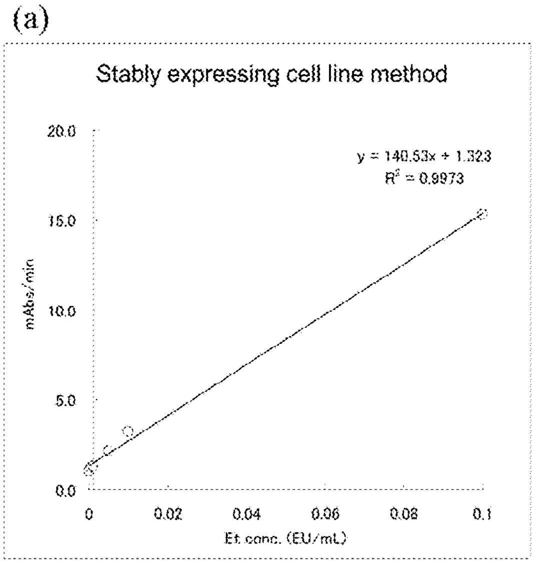
(b)
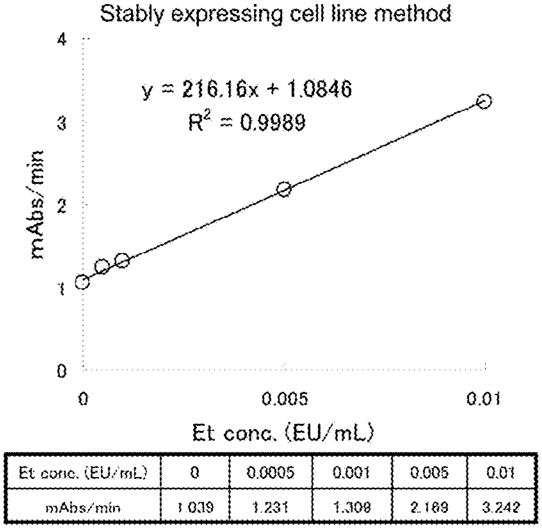
| Et conc. (EU/mL) | 0 | 0.0005 | 0.001 | 0.005 | 0.01 |
|---|---|---|---|---|---|
| mAbs/min | 1.039 | 1.231 | 1.308 | 2.169 | 3.242 |

[Fig.10]
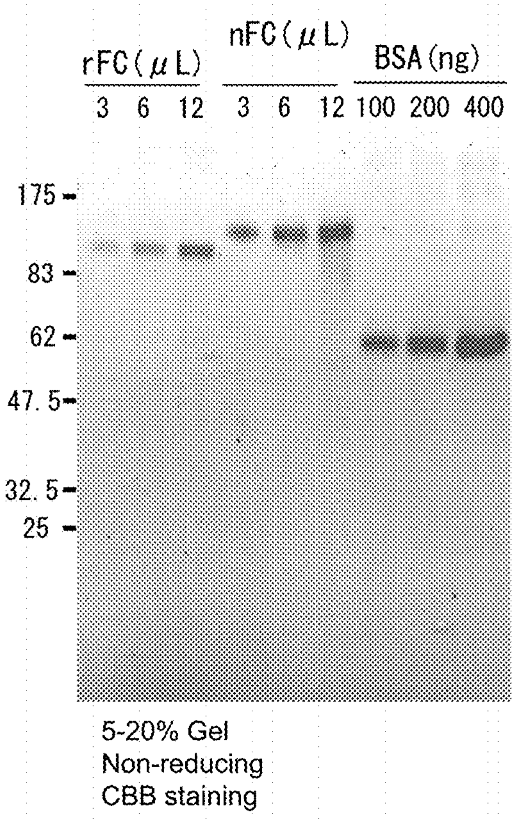

[Fig.11]
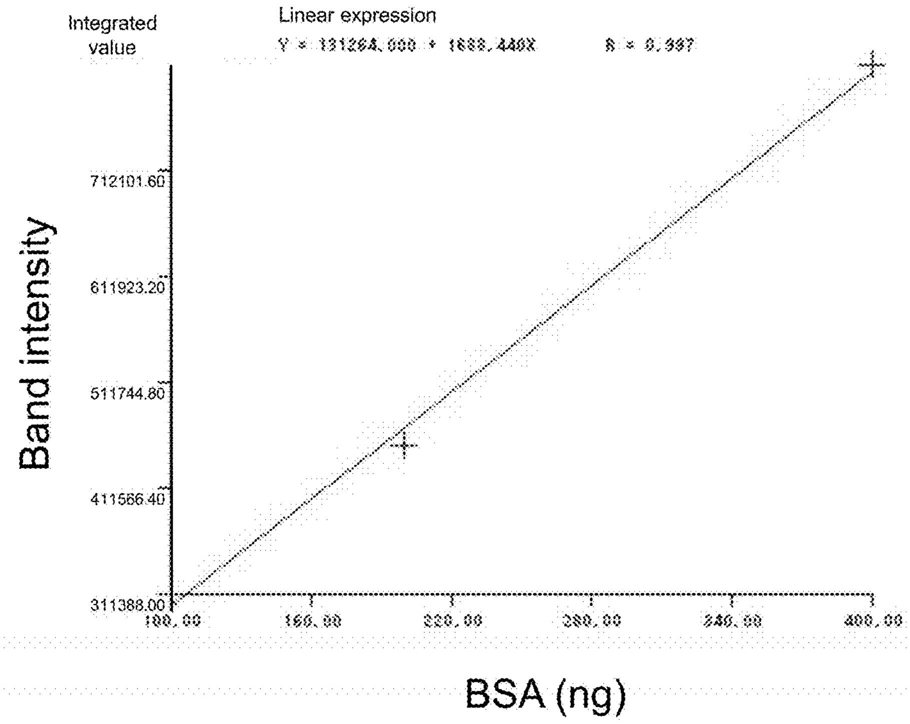
[Fig.12]
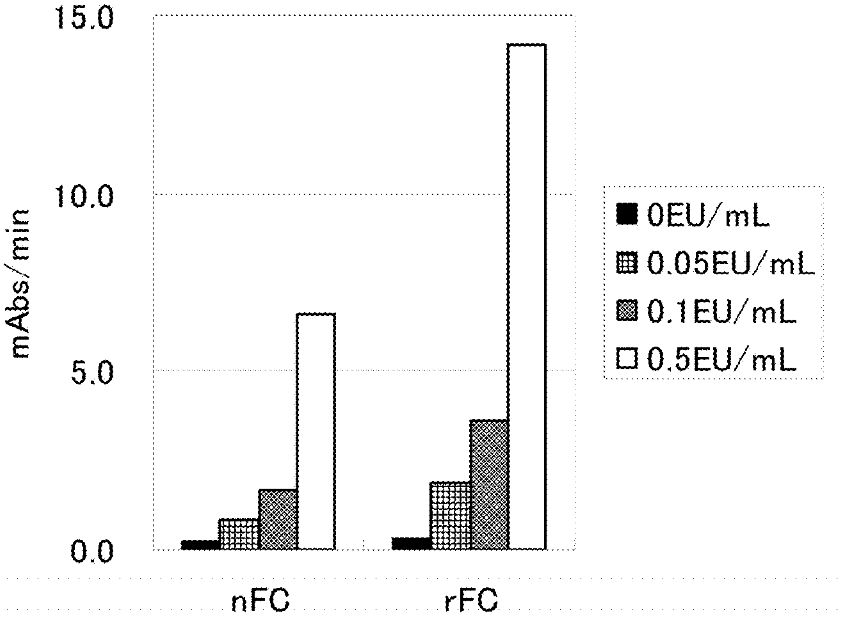

METHOD FOR PRODUCING AN EXDOTOXIN MEASURING AGENT

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

REFERENCE TO SEQUENCE LISTING

This application incorporates by reference the sequence listing submitted as ASCII text filed via EFS-Web on Sep. 9, 2013, in U.S. application Ser. No. 14/001,138. The Sequence Listing was provided as a file entitled "2013-09-09-seq 1st toya117-021apc," created on Sep. 9, 2013, and is approximately 47 kilobytes in size.

BACKGROUND OF THE INVENTION

Field of the Invention

The present invention relates to an endotoxin-measuring agent, a method for producing the measuring agent, and a method for measuring endotoxin in a sample.

Description of the Related Art

Endotoxin is a lipopolysaccharide existing on the outer membrane of the cell wall of Gram-negative bacteria, and known to be a strong pyrogen. Further, it is known that even a small amount of endotoxin causes various disease states due to bacterial infection, such as release of inflammatory cytokines due to macrophage activation and induction of endotoxin shock, in addition to fever. Therefore, detection of endotoxin in pharmaceuticals such as those for injection; water; medical equipments; and the like is important. Further, endotoxin is considered to be the main cause of shock in Gram-negative bacterial infection, and hence, the presence or absence of infection and/or a pharmaceutical effect can be judged by measuring endotoxin in the blood.

Further, it is known that infection of American horseshoe crab (*Limulus polyphemus*) with Gram-negative bacteria causes intravascular coagulation, and this phenomenon has been used for detection of endotoxin.

That is, a method for measuring endotoxin using a blood cell extract of a horseshoe crab (horseshoe crab amebocyte lysate; hereinafter also referred to as "lysate") is known (e.g., Non-patent Document 1). This method is called "limulus test", and uses a cascade reaction of various proteins existing in the lysate, which reaction is caused by contacting of endotoxin with the lysate. A schematic diagram of the cascade reaction is shown in FIG. 1.

Upon contacting of endotoxin with the lysate, factor C existing in the lysate is activated to produce active-type factor C. This active-type factor C activates factor B existing in the lysate, to produce active-type factor B. This active-type factor B then activates a proclotting enzyme existing in the lysate, to produce a clotting enzyme.

This clotting enzyme hydrolyzes a specific portion in the coagulogen molecule existing in the lysate. By this, coagulin gel is produced, to cause coagulation of the lysate. Thus, by measuring the coagulation reaction of the lysate, endotoxin can be measured.

Further, also by allowing a clotting enzyme to react with a synthetic substrate to cause color reaction, endotoxin can be measured. For example, a clotting enzyme reacts with a synthetic substrate t-butoxycarbonyl-leucyl-glycyl-arginyl-pNA (Boc-Leu-Gly-Arg-pNA) to hydrolyze its amide bond, and thereby pNA is released. Thus, by preliminarily including the synthetic substrate in the reaction system, endotoxin can be quantified by measurement of the absorbance (405 nm) of the coloring substance (pNA).

Further, it is known that the cascade reaction system can be reconstructed using factor C, factor B, and a proclotting enzyme, which were purified from lysate of a Japanese horseshoe crab (Non-patent Document 2).

Further, a case wherein a recombinant factor C derived from a Southeast Asian horseshoe crab *Carcinoscorpius rotundicauda*; and a recombinant factor B and a recombinant proclotting enzyme derived from a Japanese horseshoe crab *Tachypleus tridentatus*; were used to reconstruct the cascade reaction system is known (Patent Document 1).

Further, a system for detecting endotoxin by using a recombinant factor C derived from a Southeast Asian horseshoe crab *Carcinoscorpius rotundicauda* and a substrate that reacts with active-type factor C to release a fluorescent substance is known (Patent Document 2). This system is commercially available as an endotoxin detection system (commercial name: PyroGene (registered trademark); Lonza).

However, in order to use the lysate, or the naturally occurring factor C, factor B, and proclotting enzyme prepared therefrom, it is necessary to capture horseshoe crabs and collect blood therefrom. Hence, in view of conservation of biological resources or the like, it is difficult to supply these components unlimitedly. Therefore, a technique to easily and rapidly produce a reagent for detection of endotoxin at a low cost has been demanded.

Further, in cases where a recombinant factor C, recombinant factor B, and recombinant proclotting enzyme are used, any of the above-described cases requires 1 hour or more for the measurement, and a detection sensitivity in the order of 0.001 EU/mL has not been achieved. Therefore, a technique to rapidly and highly sensitively measure endotoxin has been demanded.

PRIOR ART DOCUMENTS

Patent Documents

[Patent Document 1] WO 2008/004674
[Patent Document 2] U.S. Pat. No. 6,849,426 B

Non-Patent Documents

[Non-patent Document 1] Iwanaga S., Curr Opin Immunol. 1993 February; 5(1): 74-82.
[Non-patent Document 2] Nakamura T. et al., J Biochem. 1986 March; 99(3): 847-57.

SUMMARY OF THE INVENTION

The present invention aims to provide a method for rapidly and highly sensitively measuring endotoxin. The present invention also aims to provide an endotoxin-measuring agent to be used in the method, and a method for producing the agent.

The present inventors discovered that endotoxin can be rapidly and highly sensitively measured by using a recombinant factor C (His-tag free), recombinant factor B and recombinant proclotting enzyme, which were derived from a Japanese horseshoe crab *Tachypleus tridentatus* and expressed using insect cells as a host, thereby completing the present invention.

That is, the present invention is as follows.

[1]

An endotoxin-measuring agent comprising the proteins (1) to (3) below, each of which is a recombinant protein obtainable by being expressed using insect cells as a host:

(1) a factor C derived from *Tachypleus tridentatus*, which factor C does not have His-tag sequence at the C-terminus;

(2) a factor B of a horseshoe crab; and (3) a proclotting enzyme of a horseshoe crab.

[2]

The measuring agent according to [1], wherein said factor B and said proclotting enzyme are derived from *Tachypleus tridentatus*.

[3]

The measuring agent according to [1] or [2], wherein said factor C is the protein (A) or (B) below; said factor B is the protein (C) or (D) below; and said proclotting enzyme is the protein (E) or (F) below:

(A) a protein comprising the amino acid sequence shown in SEQ ID NO:2;

(B) a protein comprising the amino acid sequence shown in SEQ ID NO:2 but which includes substitution, deletion, insertion, or addition of one or several amino acid residues, which protein has factor C activity;

(C) a protein comprising the amino acid sequence shown in SEQ ID NO:4;

(D) a protein comprising the amino acid sequence shown in SEQ ID NO:4 but which includes substitution, deletion, insertion, or addition of one or several amino acid residues, which protein has factor B activity;

(E) a protein comprising the amino acid sequence shown in SEQ ID NO:6;

(F) a protein comprising the amino acid sequence shown in SEQ ID NO:6 but which includes substitution, deletion, insertion, or addition of one or several amino acid residues, which protein has proclotting enzyme activity.

[4]

A method for producing the measuring agent according to any one of [1] to [3], the method comprising the steps (A) to (C) below:

(A) a step of incorporating each of the DNAs (1) to (3) below into a viral DNA:

(1) a DNA encoding a factor C derived from *Tachypleus tridentatus*, which factor C does not have His-tag sequence at the C-terminus;

(2) a DNA encoding a factor B of a horseshoe crab; and (3) a DNA encoding a proclotting enzyme of a horseshoe crab;

(B) a step of infecting insect cells with the virus into which said each DNA was incorporated; and (C) a step of allowing the insect cells infected with said each virus to express the protein encoded by said each DNA.

[5]

A method for producing the measuring agent according to any one of [1] to [3], the method comprising the steps (A) to (C) below:

(A) a step of incorporating each of the DNAs (1) to (3) below into a vector:

(1) a DNA encoding a factor C derived from *Tachypleus tridentatus*, which factor C does not have His-tag sequence at the C-terminus;

(2) a DNA encoding a factor B of a horseshoe crab; and (3) a DNA encoding a proclotting enzyme of a horseshoe crab;

(B) a step of introducing the vector, into which said each DNA was incorporated, into insect cells to incorporate said each DNA into the chromosome of the insect cells; and (C) a step of allowing the insect cells, into which said each DNA was incorporated, to express the protein encoded by said each DNA.

[6]

The method according to [4] or [5], wherein said DNA encoding factor C is the DNA (A) or (B) below; said DNA encoding factor B is the DNA (C) or (D) below; and said DNA encoding proclotting enzyme is the DNA (E) or (F) below:

(A) a DNA comprising the nucleotide sequence shown in SEQ ID NO: 1;

(B) a DNA which hybridizes with the complementary sequence of the full length or a part of the nucleotide sequence shown in SEQ ID NO:1 under stringent conditions, and encodes a protein having factor C activity.

(C) a DNA comprising the nucleotide sequence shown in SEQ ID NO:3 or 8;

(D) a DNA which hybridizes with the complementary sequence of the full length or a part of the nucleotide sequence shown in SEQ ID NO:3 or 8 under stringent conditions, and encodes a protein having factor B activity.

(E) a DNA comprising the nucleotide sequence shown in SEQ ID NO:5 or 9;

(F) a DNA which hybridizes with the complementary sequence of the full length or a part of the nucleotide sequence shown in SEQ ID NO:5 or 9 under stringent conditions, and encodes a protein having proclotting enzyme activity.

[7]

A method for measuring endotoxin in a test sample, the method comprising a step of mixing the measuring agent according to any one of [1] to [3] with the test sample and a step of measuring progress of cascade reaction.

[8]

The method according to [7], which comprises a step of adding a substrate for detection of progress of cascade reaction to a reaction system.

[9]

The method according to [8], which further comprises a step of calculating the endotoxin level in the test sample on the basis of reaction of said substrate.

By the present invention, endotoxin can be rapidly and highly sensitively measured. For example, in one embodiment of the present invention, a detection sensitivity in the order of 0.0005 EU/mL can be achieved with only 30 minutes of measurement. Further, in the present invention, the expressed recombinant factor C, recombinant factor B, and recombinant proclotting enzyme can be used without purification, and hence, an endotoxin-measuring agent comprising these recombinant proteins can be simply and rapidly produced at a low cost.

BRIEF DESCRIPTION OF THE DRAWINGS

FIG. 1 is a diagram showing the cascade reaction system in a limulus test.

FIG. 2 is a diagram showing the structure of the vector pIZ/V5-His and the position of insertion of each of the genes. The arrow in the upper part indicates the position of insertion of the genes.

FIG. 3 is a photograph showing the expression levels of various factor Cs.

FIG. 4 is a diagram showing the activities of various factor Cs. In the Figure, "EU" denotes "endotoxin unit" which is a unit denoting the amount of endotoxin; "DW" denotes "distilled water; and "mAbs/min" represents the rate of increase in the absorbance (absorbance change rate).

FIG. 5 is a photograph showing the stability of the factor C expressed by the viral method.

FIG. 6 is a photograph showing the stability of the factor C expressed by the stably expressing cell method.

FIG. 7 is a diagram showing the effect of treatment by hollow fiber membrane filtration on the reactivities of the factors expressed by the viral method.

FIG. 8 is a diagram showing the reactivity of the endotoxin-measuring agent containing the factors expressed by the viral method. In the Figure, "Et" denotes "endotoxin".

FIG. 9 is a diagram showing the reactivity of the endotoxin-measuring agent containing the factors expressed by the stably expressing cell line method. (a) The reactivity at the endotoxin concentration of 0 to 0.1 EU/mL. (b) The reactivity at the endotoxin concentration of 0 to 0.01 EU/mL.

FIG. 10 is a photograph showing the purities and concentrations of the purified recombinant factor C and the purified naturally-occurring factor C. In the Figure, "rFC" denotes "recombinant Factor C"; "nFC" denotes naturally occurring Factor C.

FIG. 11 is a calibration curve showing a relationship between band intensities and amounts of BSA. The intensities of BSA bands on the gel stained with Coomassie brilliant blue as shown in FIG. 10 were quantified with a densitometer, and plotted against the concentrations of the BSA protein, to prepare the calibration curve.

FIG. 12 is a diagram showing the activities of the purified recombinant factor C and the purified naturally-occurring factor C.

DETAILED DESCRIPTION OF THE PREFERRED EMBODIMENT

In the present invention, a series of reactions wherein endotoxin activates factor C to produce active-type factor C; the active-type factor C activates factor B to produce active-type factor B; and the active-type factor B activates a proclotting enzyme to produce a clotting enzyme; may be referred to as "cascade reaction".

(1) Endotoxin-Measuring Agent of Present Invention

The endotoxin-measuring agent of the present invention comprises factor C, factor B, and a proclotting enzyme. The factor C, factor B, and proclotting enzyme comprised in the endotoxin-measuring agent of the present invention may be hereinafter referred to as "factor C of the present invention", "factor B of the present invention" and "proclotting enzyme of the present invention", respectively. Further, the factor C, factor B, and proclotting enzyme may be collectively referred to as "factors".

All of the factor C of the present invention, factor B of the present invention, and proclotting enzyme of the present invention are recombinant proteins obtainable by being expressed using insect cells as a host.

The factor C of the present invention is a factor C derived from a Japanese horseshoe crab *Tachypleus tridentatus*. The factor C of the present invention is characterized in that it does not have a His-tag attached at the C-terminus. Further, the factor C of the present invention preferably does not have a V5-tag at the C-terminus. Further, the factor C of the present invention more preferably does not have any peptide attached at the C-terminus. Further, the factor C of the present invention especially preferably does not have any peptide attached at either terminus. An amino acid sequence of the factor C of *Tachypleus tridentatus* is shown in SEQ ID NO:2. A nucleotide sequence of the gene encoding the factor C of *Tachypleus tridentatus* is shown in SEQ ID NO:1.

The factor C of the present invention may be a variant of the protein having the amino acid sequence shown in SEQ ID NO:2 as long as the variant has the factor C activity.

The "factor C activity" means an activity by which factor C becomes active-type factor C in the presence of endotoxin, to activate factor B. The fact that the factor C of the present invention "has the factor C activity" can be confirmed, for example, by using the factor C of the present invention in combination with a suitable factor B and a suitable proclotting enzyme, and detecting the progress of the cascade reaction in the presence of endotoxin. More particularly, the protein of SEQ ID NO:4 may be used as the suitable factor B, and the protein of SEQ ID NO:6 may be used as the suitable proclotting enzyme. The progress of the cascade reaction can be measured using the later-mentioned substrate for detection.

The factor C of the present invention may be a protein comprising the amino acid sequence shown in SEQ ID NO:2 but which includes substitution, deletion, insertion, or addition of one or several amino acid residues as long as the factor C has the factor C activity. The meaning of the term "one or several" varies depending on the positions of the amino acid residues in the three-dimensional structure of the protein and the types of the amino acid residues, and, more particularly, the term means preferably 1 to 20, more preferably 1 to 10, still more preferably 1 to 5, especially preferably 1 to 3. The above-described substitution, deletion, insertion, or addition of one or several amino acids is a conservative mutation that maintains the normal function of the protein. A representative example of the conservative mutation is a conservative substitution. The conservative substitution is, for example, a mutation wherein substitution takes place mutually among Phe, Trp, and Tyr, if the substitution site is an aromatic amino acid; among Leu, Ile, and Val, if the substitution site is a hydrophobic amino acid; between Gln and Asn, if the substitution site is a polar amino acid; among Lys, Arg, and His, if the substitution site is a basic amino acid; between Asp and Glu, if the substitution site is an acidic amino acid; and between Ser and Thr, if it the substitution site an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Further, the above-described substitution, deletion, insertion, addition, inversion or the like may also include a naturally occurring mutation due to difference in the individual, strain, or species among the horseshoe crabs from which the gene was derived.

Further, the factor C of the present invention may be a protein which has a homology or identity of not less than 80%, preferably not less than 90%, more preferably not less than 95%, still more preferably not less than 97%, especially preferably not less than 99% to the full length of the amino acid sequence of factor C as described above, for example, to the full length of the amino acid sequence shown in SEQ ID NO:2, and has the factor C activity.

The gene encoding the factor C of the present invention is not particularly restricted as long as the gene encodes the factor C of the present invention as described above. The gene encoding the factor C of the present invention may be a probe prepared based on a known gene sequence, for example, a DNA which hybridizes with the complementary sequence of the full length or a part of the nucleotide sequence shown in SEQ ID NO:1 under stringent conditions and encodes a protein having the factor C activity. The term "stringent conditions" herein means conditions under which the so-called specific hybrid is formed but a non-specific hybrid is not formed. Examples of the conditions include conditions under which highly homologous DNAs hybridize to each other, for example, DNAs not less than 80% homologous, preferably not less than 90% homologous, more preferably not less than 95% homologous, still more preferably not less than 97% homologous, especially preferably not less than 99% homologous, hybridize to each other, while DNAs less homologous than the above do not hybridize to each other; and conditions under which washing is carried out once, more preferably 2 or 3 times, at a salt concentration and temperature corresponding to 60° C., 1×SSC, and 0.1% SDS; preferably 60° C., 0.1×SSC, and 0.1% SDS; more preferably 68° C., 0.1×SSC, and 0.1% SDS; which are normal washing conditions in Southern hybridization.

Further, the combinations of the codons in the gene encoding the factor C of the present invention may be modified such that the gene is optimized for being expressed in insect cell. The optimization can be carried out using, for example, a generally available contract service. The gene encoding the factor C of the present invention may be a variant of a DNA whose combinations of the codons are optimized for expression in insect cells.

The above description on variants of the gene and protein may be applied similarly to the factor B and proclotting enzyme of the present invention, and to the genes encoding those.

The factor B of the present invention is a factor B derived from a horseshoe crab. Further, the proclotting enzyme of the present invention is a proclotting enzyme derived from a horseshoe crab. Examples of the horseshoe crab include a Japanese horseshoe crab *Tachypleus tridentatus*, American horseshoe crab *Limulus polyphemus*, Southeast Asian horseshoe crab *Carcinoscorpius rotundicauda* and Southeast Asian horseshoe crab *Tachypleus gigas*. The above factors are preferably derived from, among those horseshoe crabs, the Japanese horseshoe crab *Tachypleus tridentatus.*

Amino acid sequences of the factor B and proclotting enzyme of *Tachypleus tridentatus* are shown in SEQ ID NOs:4 and 6, respectively. Nucleotide sequences of the genes encoding the factor B and proclotting enzyme of *Tachypleus tridentatus* are shown in SEQ ID NOs:3 and 5, respectively.

The factor B of the present invention may be a variant of the factor B of any of the above-described horseshoe crabs, for example, a variant of the protein having the amino acid sequence shown in SEQ ID NO:4, as long as the factor B of the present invention has the factor B activity. Further, the gene encoding the factor B of the present invention is not particularly restricted as long as the gene encodes the factor B of the present invention as described above. The above description on factor C is also applied mutatis mutandis to the variants of the gene and protein.

The "factor B activity" means an activity by which factor B becomes active-type factor B in the presence of active-type factor C, to change a proclotting enzyme into its active form, a clotting enzyme. The fact that the factor B of the present invention "has the factor B activity" can be confirmed, for example, by using the factor B of the present invention in combination with a suitable factor C and a suitable proclotting enzyme, and detecting the progress of the cascade reaction in the presence of endotoxin. More particularly, the protein of SEQ ID NO:2 may be used as the suitable factor C, and the protein of SEQ ID NO:6 may be used as the suitable proclotting enzyme. The progress of the cascade reaction can be measured using the later-mentioned substrate for detection.

The proclotting enzyme of the present invention may be a variant of the proclotting enzyme of any of the above-described horseshoe crabs, for example, a variant of the protein having the amino acid sequence shown in SEQ ID NO:6, as long as the proclotting enzyme of the present invention has the proclotting enzyme activity. Further, the gene encoding the proclotting enzyme of the present invention is not particularly restricted as long as the gene encodes the proclotting enzyme of the present invention as described above. The above description on factor C is also applied mutatis mutandis to the variants of the gene and protein.

The "proclotting enzyme activity" means an activity by which a proclotting enzyme is changed to a clotting enzyme in the presence of active-type factor B, to react with the later-mentioned substrate for detection. The "activity to react with a substrate for detection" means, for example, an activity to react with coagulogen to cause coagulation, and an activity to react with Boc-Leu-Gly-Arg-pNA to release pNA. The fact that the proclotting enzyme of the present invention "has the proclotting enzyme activity" can be confirmed, for example, by using the clotting enzyme of the present invention in combination with a suitable factor C and a suitable factor B, and detecting the progress of the cascade reaction in the presence of endotoxin. More particularly, the protein of SEQ ID NO:2 may be used as the suitable factor C, and the protein of SEQ ID NO:4 may be used as the suitable factor B. The progress of the cascade reaction can be measured using the later-mentioned substrate for detection.

To the factor B of the present invention and/or the proclotting enzyme of the present invention, an arbitrary peptide or the like may be added as long as the factors have the factor B activity and the proclotting enzyme activity, respectively. Examples of such a peptide include tag sequences such as His-tag and V5-tag. Similarly to the factor C of the present invention, the factor B of the present invention and/or the proclotting enzyme of the present invention to be employed may be any of those wherein His-tag is not added to the C-terminus, those wherein V5-tag is not added to the C-terminus, those wherein no peptide is added to the C-terminus at all, and those wherein no peptide is added to either terminus at all.

Further, the combinations of the codons in the gene encoding the factor B of the present invention and/or the gene encoding the proclotting enzyme of the present invention may be modified such that the gene(s) is/are optimized for being expressed in insect cells. Examples of the DNA that encodes the factor B of SEQ ID NO:4 and has combinations of the codons optimized for expression in insect cells include the DNA of SEQ ID NO:8. Examples of the DNA that encodes the proclotting enzyme of SEQ ID NO:6 and has combinations of the codons optimized for expression in insect cells include the DNA of SEQ ID NO:9. Each of the gene encoding the factor B of the present invention and/or the gene encoding the proclotting enzyme of the present invention may be a variant of a DNA whose combinations of the codons are optimized for expression in insect cells.

The endotoxin-measuring agent of the present invention may consist of the factor C of the present invention, the factor B of the present invention, and the proclotting enzyme of the present invention.

The endotoxin-measuring agent of the present invention may comprise a substrate for detection of the progress of the cascade reaction. In the present invention, such a substrate may be referred to as "substrate for detection".

Examples of the substrate for detection include coagulogen. Due to contact of coagulogen with a clotting enzyme, coagulation occurs to produce coagulin. The progress of the coagulation reaction may be assayed by measuring the turbidity of the reaction solution. Coagulogen can be recovered from a horseshoe crab blood cell extract (lysate). Also, because a nucleotide sequence of the gene encoding coagulogen has been clarified (Miyata, et al., PROTEIN, NUCLEIC ACID AND ENZYME, Extra Edition, No. 29, pp. 30-43 (1986)), coagulogen can be produced according to a conventional method by genetic engineering.

As the substrate for detection, a synthetic substrate may also be used. The synthetic substrate is not particularly restricted as long as the substrate has a property suitable for detection, such as a property by which catalytic reaction of a clotting enzyme causes development of color or emission of fluorescence. Examples of the synthetic substrate include substrates represented by the general formula X—Y—Z (wherein X represents a protecting group, Y represents a peptide, and Z represents a dye bound to Y via an amide bond). In cases where endotoxin exists in the reaction system, catalytic reaction of a clotting enzyme, which is yielded as a result of the cascade reaction, cleaves the amide bond between Y and Z, to release the dye Z, leading to development of color or emission of fluorescence. The protecting group X is not particularly restricted, and a known protecting group for peptides may be suitably used. Examples of such a protecting group include the t-butoxycarbonyl group and the benzoyl group. The dye Z is not particularly restricted, and may be either a dye which can be detected under visible light or a fluorescent dye. Examples of the dye Z include pNA (para-nitroaniline), MCA (7-methoxycoumarin-4-acetic acid), DNP (2,4-dinitroaniline), and Dansyl dyes. Examples of the peptide Y include Leu-Gly-Arg (LGR), Ile-Glu-Gly-Arg (IEGR) (SEQ ID NO:12), and Val-Pro-Arg (VPR). The released dye Z may be measured by a method selected depending on the property of the dye.

Further, the endotoxin-measuring agent of the present invention may also comprise a component other than the factors and the substrate for detection, as long as the agent can be used for measurement of endotoxin. Such a component is not particularly restricted, and may be selected in consideration of preservability, ease of handling, and stability of the factors and the substrate for detection. The endotoxin-measuring agent of the present invention may comprise, for example, a pH-buffering agent and/or salt. Examples of the pH-buffering agent include HEPES buffer, MES buffer, Tris buffer, and GTA wide-range buffer. Organic solvents such as alcohols, esters, ketones, and amides may also be comprised in the endotoxin-measuring agent of the present invention.

The endotoxin-measuring agent of the present invention may be formulated into an arbitrary form including, for example, a solid form, liquid form, and gel form. For the formulation, additives normally used as formulation carriers such as vehicles; binders; disintegrants; lubricants; stabilizers; correctives; diluents; surfactants; and solvents may be used. The endotoxin-measuring agent of the present invention may be used for measuring endotoxin as it is, or after being diluted, dispersed, or dissolved in water, physiological saline, buffer, or the like. Needless to say, the resulting formulation obtained by such dilution, dispersion, or dissolution is also within the scope of the endotoxin-measuring agent of the present invention.

In the endotoxin-measuring agent of the present invention, the factors and the other components may exist as a mixture(s) or may separately exist. For example, the factors may be mixed at an arbitrary ratio to be formulated, or may be separately formulated.

The concentrations of the factors and the other components in the endotoxin-measuring agent of the present invention are not particularly restricted, and preferably adjusted such that the concentrations are within the later-mentioned preferred ranges when endotoxin is measured. The concentration of each of the factors in the endotoxin-measuring agent of the present invention (in terms of the solution prepared before contacting with the test sample) is, for example, preferably 20 to 100 μg/mL, more preferably 40 to 80 μg/mL, especially preferably about 60 μg/mL.

The endotoxin-measuring agent of the present invention may be provided as an endotoxin-measuring kit. The endotoxin-measuring kit is not particularly restricted as long as the kit contains the endotoxin-measuring agent of the present invention.

(2) Method for Producing Endotoxin-Measuring Agent of Present Invention

The factors to be comprised in the endotoxin-measuring agent of the present invention can be produced by being expressed using insect cells as a host.

The insect cells are not particularly restricted as long as the cells can express the factors, and cells normally used for expression of a heterologous protein may be suitably used. Examples of such insect cells include Sf9, Sf21, SF+, and High-Five. The insect cells are preferably Sf9.

The culture conditions under which the insect cells are cultured are not particularly restricted as long as the insect cells can be cultured under the conditions, and culture conditions normally used for culturing insect cells may be used after, if necessary, appropriately modified. For example, as a culture medium, one normally used for culturing insect cells may be used. Examples of such a medium include commercially available serum-free media for insect cells. More particularly, Sf900 II medium (Invitrogen) or the like may be suitably used. The cultivation may be carried out, for example, at 27° C. to 28° C. with shaking.

The method for expressing the factors using insect cells as a host is not particularly restricted as long as the factors can be expressed thereby, and a method normally used for expression of a heterologous protein can be suitably used. For example, each factor can be expressed by infecting insect cells with a virus into which a gene encoding the factor was incorporated (viral method). Alternatively, each factor can be expressed by introducing a vector, into which a gene encoding the factor was incorporated, into insect cells, thereby incorporating the gene into the chromosome of the host (stably expressing cell line method).

<Viral Method>

The virus to be used in the viral method is not particularly restricted as long as insect cells can be infected with the virus and the factors can be expressed thereby, and a virus normally used for expression of a protein in insect cells can be suitably used. Examples of such a virus include baculovirus. The baculovirus is preferably nucleopolyhedrovirus (NPV). Examples of the NPV include AcNPV (*Autographa californica* NPV) and BmNPV (*Bombix mori* NPV). The NPV is preferably AcNPV.

Introduction of the nucleic acid into the virus can be carried out by a conventional method, for example, by homologous recombination using a transfer vector. Examples of the transfer vector include pPSC8 (Protein Sciences), pFastBac (Invitrogen), and pVL1393 (Pharmingen). The transfer vector is preferably pPSC8.

By infecting, by a conventional method, insect cells with a virus into which the gene encoding each factor was incorporated, insect cells that harbor the virus and express the factor can be obtained.

<Stably Expressing Cell Line Method>

By incorporating the gene encoding each factor into the chromosome of insect cells, a stably expressing cell line, which stably expresses the factor, can be obtained. The method of construction of the stably expressing cell line is not particularly restricted, and the construction can be carried out by a conventional method. For example, the stably expressing cell line can be constructed using the pIZ/V5-His vector (Invitrogen) according to the manual.

In any case, the expressing cells are constructed such that the expressed factor C has the C-terminus to which Histag is not attached. Further, in cases where each factor is to be expressed without addition of any peptide, which is not restricted to His-tag at the C-terminus of the factor C, the expressing cells may be constructed such that no peptide is added.

In any case, the factors may be expressed together by a single type of expressing cells, or expressing cells may be constructed for each factor to express the respective factors separately.

Whether or not each factor is expressed can be confirmed by measuring the activity of the factor. Whether or not each factor is expressed can also be confirmed by measuring the amount of mRNA transcribed from the gene encoding the factor, or by detecting the factor by Western blotting using an antibody.

Each expressed factor may be recovered as a solution containing the factor, to be used as a component of the endotoxin-measuring agent of the present invention. The solution containing the factor may be, for example, a culture broth, culture supernatant, or cell extract, or a mixture thereof. Each factor may be used either after purification or without purification. In the present invention, an endotoxin-measuring agent having a sufficiently high performance can be provided even by using cell culture supernatant containing each expressed factor as it is without purification of the factor. In cases where each factor is to be purified, the purification may be carried out, for example, by a known method used for purification of a protein. Examples of such a method include ammonium sulfate precipitation, gel filtration chromatography, ion-exchange chromatography, hydrophobic interaction chromatography, and hydroxyapatite chromatography. In cases where a tag such as His-tag is attached to each factor, the factor may also be purified by affinity chromatography using affinity against the tag.

In cases where each factor was produced by the viral method, the virus is preferably eliminated. The method of elimination of the virus is not particularly restricted, and the elimination may be carried out by a conventional method. For example, the virus may be eliminated through a hollow-fiber filtration membrane having a pore size of 500 kDa.

(3) Method of Present Invention for Measuring Endotoxin

By mixing the endotoxin-measuring agent of the present invention with a test sample, the cascade reaction proceeds in cases where the test sample contains endotoxin. By measuring the progress of the cascade reaction, the endotoxin in the test sample can be measured. That is, the present invention provides a method for measuring endotoxin in a test sample, which method comprises a step of mixing the endotoxin-measuring agent of the present invention with a test sample, and a step of measuring the progress of the cascade reaction (hereinafter referred to as "first embodiment").

In the first embodiment, each factor comprised in the endotoxin-measuring agent of the present invention may have been contained in the reaction system from the beginning of the step of mixing the endotoxin-measuring agent of the present invention with a test sample, or may be sequentially added to the reaction system.

For example, the step of mixing the endotoxin-measuring agent of the present invention with a test sample may comprise the following steps (A) to (C):

(A) a step of adding the factor C of the present invention to the reaction system;

(B) a step of adding the factor B of the present invention to the reaction system; and (C) a step of adding the proclotting enzyme of the present invention to the reaction system.

Steps (A) to (C) may be carried out separately, partially at the same time, or totally at the same time. Steps (A) to (C) may be carried out in an arbitrary order. For example, Step (A) may be followed by Step (B), which may then be followed by Step (C).

In the first embodiment, the progress of the cascade reaction can be measured by adding a substrate for detection to the reaction system and then measuring the reaction of the substrate (coloring, coagulation, or the like). The substrate for detection may have been contained in the reaction system from the beginning of the step of mixing the endotoxin-measuring agent of the present invention with a test sample, or may be added to the reaction system during the progress or after completion of the step. The first embodiment, of course, includes cases where the endotoxin-measuring agent of the present invention which preliminarily contains a substrate for detection is employed.

As long as the cascade reaction proceeds in cases where endotoxin is contained in the test substance, the factor B and the proclotting enzyme of the present invention themselves may not necessarily contact with the test sample. That is, another embodiment of the method of the present invention for measuring endotoxin (hereinafter referred to as "second embodiment") is a method for measuring endotoxin in a test substance, which method comprises Steps (A) to (D) below.

(A) a step of mixing the factor C of the present invention with a test sample;

(B) a step of mixing the factor B of the present invention with the factor C after the mixing thereof in Step A;

(C) a step of mixing the proclotting enzyme of the present invention with the factor B after the mixing thereof in Step B; and (D) a step of measuring the progress of the cascade reaction.

In the second embodiment, Steps (A) to (D) may proceed separately, partially at the same time, or totally at the same time. For example, after beginning Step A, the factor B and/or proclotting enzyme may be added to the reaction system during the progress or after completion of the step. Alternatively, after beginning Step B, the proclotting enzyme may be added to the reaction system during the progress or after completion of the step. Alternatively, all the 3 factors may be contained in the reaction system from the beginning of Step A. Alternatively, for example, the factor C after the contacting in Step A may be recovered to be used in Step B, and the factor B after the contacting in Step B may be recovered to be used in Step C.

In the second embodiment, the progress of the cascade reaction may be measured by adding a substrate for detection to the reaction system and then measuring reaction of the substrate (coloring, coagulation, or the like). The substrate for detection may be contained in the reaction system from the beginning of Step A, or may be added to the reaction system during the progress or after completion of each step.

The method of the present invention for measuring endotoxin may comprise another arbitrary step as long as the cascade reaction proceeds in cases where the test sample contains endotoxin. For example, the method of the present invention for measuring endotoxin may comprise a step of adding a substrate for detection to the reaction system, or a step of mixing a clotting enzyme produced by the cascade reaction with a substrate for detection. Further, for example, the method of the present invention for measuring endotoxin may comprise a step of calculating the endotoxin level in the test sample on the basis of reaction of the substrate for detection.

In the method of the present invention for measuring endotoxin, the reaction is preferably carried out in an aqueous solvent such as water or a buffer.

In the method of the present invention for measuring endotoxin, the concentration of each factor in the reaction solution is not particularly restricted as long as the cascade reaction proceeds in cases where endotoxin is contained in the test sample, and may be set appropriately depending on the property of the factor and/or the like. For example, the concentration of each factor is usually 10 to 50 μg/mL, preferably 20 to 40 μg/mL, more preferably about 30 μg/mL, in terms of the final concentration.

In the method of the present invention for measuring endotoxin, the concentration of the substrate for detection in the reaction solution is not particularly restricted as long as the cascade reaction proceeds in cases where endotoxin is contained in the test sample, and may be set appropriately depending on the property of the substrate for detection and/or the like. For example, in cases where the substrate for detection is a synthetic substrate, the concentration of the substrate for detection is usually 0.001 mM to 100 mM, preferably 0.01 mM to 10 mM, in terms of the final concentration.

In any embodiment, the reaction system may contain an arbitrary component(s) other than the endotoxin-measuring agent in the first embodiment or the factors in the second embodiment, substrate for detection, and test sample, as long as the cascade reaction proceeds in cases where endotoxin is contained in the test sample. For example, the reaction system may contain a pH-buffering agent and/or salt. Examples of the pH-buffering agent include HEPES buffer, MES buffer, Tris buffer, and GTA wide-range buffer. Organic solvents such as alcohols, esters, ketones, and amides may also be contained in the reaction system.

The pH of the reaction solution is not particularly restricted as long as the cascade reaction proceeds in cases where endotoxin is contained in the test sample, and may be set appropriately depending on the property of each factor. For example, the pH of the reaction solution is usually 5 to 10, preferably 7 to 8.5.

The reaction temperature is not particularly restricted as long as the cascade reaction proceeds in cases where endotoxin is contained in the test sample, and may be set appropriately depending on the property of each factor. The reaction temperature is, for example, usually 10° C. to 80° C., preferably 20° C. to 50° C. For example, the reaction temperature may be room temperature.

The reaction time is not particularly restricted, and may be set appropriately depending on conditions such as the property of each factor and the reaction temperature. The reaction time is, for example, usually 5 minutes to 1 hour, preferably 15 minutes to 45 minutes. For example, the reaction time may be 30 minutes.

In any embodiment, during the process of reaction, the test sample, factors, and other components may be additionally added, individually or in an arbitrary combination, to the reaction system. These components may be added at once or in a plurality of times, or may be added continuously. Constant conditions may be employed from the beginning of the reaction to the end of the reaction, or conditions may be changed during the process of reaction.

By measuring reaction of the substrate for detection (coloring, coagulation, or the like), the progress of the cascade reaction due to existence of endotoxin can be measured, and hence the endotoxin in the test substance can be measured. The reaction of the substrate for detection (coloring, coagulation, or the like) may be measured by a method depending on the substrate for detection employed.

In cases where the measurement of endotoxin is carried out quantitatively, an endotoxin standard sample whose concentration is known may be used to obtain a correlation data between the endotoxin level and the degree of reaction of the substrate for detection (degree of coloring, coagulation, or the like), and, endotoxin existing in the test sample may be quantified on the basis of the correlation data. The correlation data may be, for example, a calibration curve. The quantification may be carried out either by the kinetic method or by the end point method.

The test sample to be subjected to the measurement of endotoxin is not particularly restricted, and examples thereof include medical water, pharmaceuticals, infusion solutions, blood preparations, medical equipments, medical apparatuses, cosmetics, foods and beverages, environmental samples (e.g., airs, rivers, and soils), biological components (e.g., bloods, body fluids, and tissues), naturally occurring proteins, recombinant proteins, nucleic acids, and carbohydrates. The test sample may be subjected to the measurement of endotoxin by mixing, dispersing, or dissolving the test sample as it is or an extract or washing solution of the test sample in a reaction system.

EXAMPLES

The present invention will now be described by way of Examples more particularly. However, these are merely examples of the present invention, and the scope of the present invention is not limited to these.

Example 1: Production of Endotoxin-Measuring Agent of Present Invention (1-1) Method Using Virus (Hereinafter Referred to as "Viral Method")

In the present Example, a recombinant baculovirus into which the gene encoding each of factor C, factor B, and a proclotting enzyme was incorporated was used to express the factor in insect cells, and an endotoxin-measuring agent was thereby produced.

(1-1-1) Preparation of Recombinant Baculovirus

As a DNA encoding His-tag-attached factor C (His-tag-attached factor C gene), the DNA of SEQ ID NO:7 was totally synthesized using a generally available contract service (TAKARA BIO INC.). The His-tag-attached factor C is the factor C of a Japanese horseshoe crab shown in SEQ ID NO:2 wherein a 6×His-tag is attached to the C-terminus. The DNA was inserted between the recognition sites of restriction enzymes NruI and SmaI of a transfer vector pPSC8 (Protein Sciences), to obtain a vector for recombination. Using the vector for recombination, the His-tag-attached factor C gene was incorporated into a baculovirus AcNPV, to prepare a recombinant baculovirus.

Further, using a primer FC-N-Pst (SEQ ID NO:10) and a primer FC-notag-R-Bam (SEQ ID NO:11), and the above-described DNA encoding the His-tag-attached factor C as a template, PCR was carried out to prepare a DNA encoding factor C wherein the nucleotide sequence encoding the His-tag sequence at the 3'-end was removed (His-tag-free factor C gene). The DNA encodes the Japanese horseshoe crab factor C shown in SEQ ID NO:2, wherein no His tag is attached at the C-terminus. Also for the His-tag-free factor C gene, a recombinant baculovirus was prepared by the same method as described above.

As a DNA encoding factor B (factor B gene), the DNA of SEQ ID NO:8 was totally synthesized using a generally available contract service (TAKARA BIO INC.). The DNA encodes the Japanese horseshoe crab factor B shown in SEQ ID NO:4 (His-tag free), and the combinations of its codons are optimized for expression in insect cells. Also for the factor B gene, a recombinant baculovirus was prepared by the same method as described above. However, the position of insertion in the pPSC8 vector was between the recognition sites of restriction enzymes PstI and KpnI.

As a DNA encoding the proclotting enzyme (proclotting enzyme gene), the DNA of SEQ ID NO:9 was totally synthesized using a generally available contract service (TAKARA BIO INC.). The DNA encodes the Japanese horseshoe crab proclotting enzyme shown in SEQ ID NO:6 (His-tag free), and the combinations of its codons are optimized for expression in insect cells. Also for the proclotting enzyme gene, a recombinant baculovirus was prepared by the same method as described above. However, the position of insertion in the pPSC8 vector was between the recognition sites of restriction enzymes XbaI and BglII.

(1-1-2) Infection of Insect Cells (Sf9 Cells) with Recombinant Baculovirus

Sf9 cells (Novagen) were inoculated in a medium at $1.5\times10^6$ cells/mL, and the recombinant baculovirus, into which the DNA encoding the His-tag-attached factor C was introduced, was added to the medium, to infect the cells with the virus. As the medium for the Sf9 cells, Sf900 II medium (Invitrogen) supplemented with antibiotics (antibiotics-antifungal agents (×100); Invitrogen) (final concentration, ×1) (1 L) was used. The multiplicity of infection (MOI) of the virus was set to 1.0. Thereafter, the obtained cells were cultured at 28° C. for 48 hours with shaking.

Similarly, Sf9 cells were infected with the virus into which the DNA encoding the His-tag-free factor C was introduced.

Further, Sf9 cells were infected also with each of the virus to which the DNA encoding the factor B was introduced and the virus to which the DNA encoding the proclotting enzyme was introduced. In these cases, MOI was set to 0.5, and the culturing time was 72 hours.

(1-1-3) Recovery of Solution of Expressed Recombinant Protein

Each of the culture broths obtained after the above culturing was centrifuged at 4° C. at 3000×g for 30 minutes to obtain the supernatant, which was then stored at −80° C.

(1-1-4) Removal of Impurities and Viruses from Recombinant Protein Solution

Each of the supernatants which had been stored frozen as described above was thawed, and applied to a filter having a pore size of 0.1 μm (Cup Filter (Millipore)). Filtration was carried out with suction, and the solution which had passed through the filter was recovered. Each recovered supernatant was applied to a hollow fiber filtration membrane having a pore size of 500 kDa (polyether sulfone hollow fiber membrane; Spectrum Labs) and filtered using the Kros Flow TFF pump filtration system (Spectrum Labs). Each solution which had passed through the membrane was recovered.

(1-1-5) Preparation of Reagent

At 4° C., 560 mL of each solution obtained in the above (1-1-4) (wherein factor C, factor B, or proclotting enzyme is contained), 134 mL of distilled water, 126 mL of 6.66 mM aqueous solution of a synthetic substrate (Boc-Leu-Gly-Arg-pNA) (final concentration, 0.3 mM) and 560 mL of 15% aqueous dextran solution (final concentration, 3%) were mixed together. This mixture was aliquoted in 5 mL-volumes into vials and freeze-dried, to provide the endotoxin-measuring agent 1.

(1-2) Method Using Plasmid (Hereinafter Also Referred to as "Stably Expressing Cell Line Method")

In the present Example, a gene encoding each of the factor C, factor B, and proclotting enzyme was incorporated into the chromosome of insect cells to construct a stably expressing cell line, and each factor was then expressed, thereby producing an endotoxin-measuring agent.

(1-2-1) Preparation and Cultivation of Stably Expressing Cell Line

Each of the His-tag-free factor C gene, factor B gene (SEQ ID NO:8), and proclotting enzyme gene (SEQ ID NO:9) used in the above-described viral method was introduced into Sf9 cells (Invitrogen) using the pIZ vector kit (Invitrogen).

More particularly, each of the DNAs was firstly incorporated between the EcoRV and MluI recognition sites in a vector pIZ/V5-His comprised in the kit, and the resulting each vector was mixed with Cellfectin comprised in the kit, followed by introduction of the vector into Sf9 cells. The position of incorporation of the DNAs in pIZ/V5-His, and the like are shown in FIG. 2. In the region indicated by a thick arrow shown at the top in FIG. 2, each one of the DNAs was incorporated. As the medium for the Sf9 cells, Sf900 III medium (Invitrogen) supplemented with antibiotics (antibiotics-antifungal agents (×100); Invitrogen) (final concentration, ×1) and Zeocin antibiotic (Invitrogen) (final concentration, 50 μg/mL) was used. The density of the thus obtained cell line, into which each DNA was introduced, was adjusted to $6 \times 10^5$ cells/mL (1 L) in the medium, and the cells were cultured at 28° C. for 96 hours with shaking.

It should be noted that, although a His tag sequence is contained in pIZ/V5-His, all of the above described DNAs have a stop codon, so that all of the factor C, factor B, and proclotting enzyme are expressed without addition of His-tag.

(1-2-2) Recovery of Solution of Recombinant Protein, Removal of Impurities, and Preparation of Reagent Each culture broth obtained after the above-described culturing was processed in the same manner as described in "(1-1-3) Recovery of Solution of Expressed Recombinant Protein", "(1-1-4) Removal of Impurities and Viruses from Recombinant Protein Solution" and "(1-1-5) Preparation of Reagent" for the viral method. However, the process of filtration using a hollow fiber filtration membrane in "(1-1-4) Removal of Impurities and Viruses from Recombinant Protein Solution" was not carried out. The thus obtained measuring agent was provided as the endotoxin-measuring agent 2.

Example 2: Properties and the Like of Expressed Proteins (2-1) Comparison of Expression Level of Factor C The expression level was compared among the His-tag-free factor Cs obtained by the viral method and the stably expressing cell line method, and the His-tag-attached factor C obtained by the viral method.

The expression level was evaluated by sampling 0.5, 1.5, 5, or 15 μL of the solution corresponding to the one after the filtration and before the preparation of the reagent in Example 1 and subjecting the sampled solutions to 5-20% polyacrylamide gel electrophoresis (under non-reducing conditions) in the presence of SDS and then to Western blotting using an anti-factor C antibody (2C12, obtained from Prof. Shun-ichiro Kawabata, Department of Biology, Graduate School of Sciences, Kyushu University).

The results are shown in FIG. 3. The results indicate that the expression levels of the His-tag-free factor Cs were lower than the expression level of the His-tag-attached factor C. Further, the intensities of the bands on the Western blot in FIG. 3 were measured using a densitometer, and, the volume ratio of each solution with which equal concentrations of the factor Cs are attained was calculated on the basis of relative values of the measured intensities. The volume ratio was 50 as for the His-tag free factor C obtained by the viral method, 17 as for the His-tag free factor C obtained by the stably expressing cell line method, and 7 as for the His-tag-attached factor C obtained by the viral method.

(2-2) Comparison of Activity of Factor C

The proclotting enzyme-activating capacity of each of the factor C solutions was studied using an equal amount of factor C.

More particularly, each of the His-tag-attached factor C solution obtained by the viral method (0.7 μL or 5 μL), His-tag-free factor C solution obtained by the viral method (5 μL), and His-tag-free factor C solution obtained by the stably expressing cell line method (1.7 μL) was placed in a well of a 96-well plate. Thereafter, the factor B-containing solution (5 μL) and the proclotting enzyme-containing solution (5 μL) obtained after the filtration through the 0.1 μm filter in (1-1-4) in the viral method in Example 1, and Boc-Leu-Gly-Arg-pNA (final concentration, 0.3 mM), Tris-HCl (pH 8.0) (final concentration, 100 mM), and 50 μL of endotoxin (product name "USP-Reference Standard Endotoxin" (USP-RSE); commercially available from Seikagaku Biobusiness Corporation) (sample concentration: 0, 0.05, or 0.5 EU/mL) were added to each well such that the total volume in the well became 100 μL, and mixed together, followed by incubation at 37° C. for 3 hours, during which the absorbance at 405 nm was measured with time. As a negative control, distilled water was used. The rate of increase in the absorbance (the absorbance change rate) reflects the proclotting enzyme-activating capacity. The term "EU" means the "endotoxin unit", which is a unit representing the amount of endotoxin (this also applies hereinafter).

The results are shown in FIG. 4. In FIG. 4, "DW" means distilled water; "Virus+His tag (×1)" means the His-tag-attached factor C solution obtained by the viral method (0.7 μL); "Virus+His tag (×7)" means the same solution (5 μL); "Virus No tag (×1)" means the His-tag free factor C solution obtained by the viral method; and "Stable Sf9 No tag (×1)" means the His-tag free factor C solution obtained by the stably expressing cell line method.

As a result, activation of the proclotting enzyme was not observed or hardly observed in the His-tag-attached factor C solution containing the equal amount of factor C (0.7 μL), and even in the solution containing about 7 times the amount of factor C (5 μL). On the other hand, the His-tag-free factor C showed a remarkable proclotting enzyme-activating capacity irrespective of whether it was obtained by the viral method or by the stably expressing cell line method.

From the above results, it was shown that a recombinant factor C molecule expressed without addition of His-tag sequence has a much stronger proclotting enzyme-activating capacity than a recombinant factor C molecule expressed with addition of His-tag sequence. Further, it was shown that each of the expressed proteins can be used without purification, in the state where the protein is contained in the culture supernatant.

(2-3) Comparison of Stability of Expressed Factor C (2-3-1) Stability of Factor C Expressed by Viral Method In the step of culturing the virus-infected cells at 28° C. with shaking in (1-1-2) in the viral method in Example 1, the supernatant was recovered after 48 hours, 72 hours, and 96 hours of cultivation, and each recovered supernatant was subjected to 5-20% polyacrylamide gel electrophoresis (under non-reducing conditions) in the presence of SDS, followed by evaluation of the remaining amount of the factor C by Western blotting using the anti-factor C antibody (2C12, which is the same as the one used above). Further, sampling and analysis were separately carried out in the same manner for the supernatant obtained by adding a protease inhibitor (leupeptin at a final concentration of 0.5 μg/mL+pepstatin A at a final concentration of 0.7 μg/mL) to the culture broth after 24 hours of the infection with the virus.

The results are shown in FIG. 5. As a result, it was shown that the factor C expressed by the viral method was decomposed with time during the cultivation. Further, it was shown that decomposition of the factor C also occurred to some extent in the case where the protease inhibitor was added.

(2-3-2) Stability of Factor C Expressed by Stably Expressing Cell Line Method

Similarly, in the step of culturing the stably expressing cell line at 28° C. with shaking in (1-2-1) in the stably expressing cell line method in Example 1, the supernatant was recovered after 72 hours, 96 hours, 120 hours, 144 hours, and 168 hours of cultivation, and each recovered supernatant was subjected to 5-20% polyacrylamide gel electrophoresis (under non-reducing conditions) in the presence of SDS, followed by evaluation of the remaining amount of the factor C by Western blotting using the anti-factor C antibody (2C12, which is the same as the one used above). Further, the supernatant obtained after 48 hours of cultivation by the viral method was also applied.

The results are shown in FIG. 6. As a result, the factor C expressed by the stably expressing cell line method has not been decomposed in the absence of a protease inhibitor even after 168 hours of cultivation. By this, it was shown that use of the stable expressing cell line method can prevent decomposition of factor C.

(2-4) Study on Whether Treatment by Hollow Fiber Membrane Filtration is Necessary Whether the treatment by a hollow fiber filtration membrane in (1-1-4) in the viral method is necessary was studied. Using each solution sampled before filtration through the hollow fiber membrane in (1-1-4) and each solution sampled after filtration therethrough (3 lots) in (1-1-4), the rate of increase in the absorbance (the absorbance change rate) was measured in the same manner as in the above (2-2), by adding endotoxin (USP-RSE) to a final concentration of 0 or 0.05 EU/mL.

The results are shown in FIG. 7. In FIG. 7, “unfiltered solution” means a solution remained in the hollow fiber membrane cartridge without being filtered. In the cases where each solution sampled after filtration through the hollow fiber membrane was used, the degree of activation of the proclotting enzyme was low when the concentration of endotoxin was 0 EU/mL (in other words, the blank value upon endotoxin measurement was low), and that is, an excellent result was obtained. By contrast, it was revealed that, in the cases where each solution sampled before filtration through the hollow fiber membrane (“before filtration” or “unfiltered solution”) was used, the degree of activation of the proclotting enzyme was high even in the cases of 0 EU/mL of endotoxin, which leads to a high blank value upon endotoxin measurement.

By contrast, by the stably expressing cell line method, the degree of activation of the proclotting enzyme in the case of 0 EU/mL of endotoxin (the blank value upon endotoxin measurement) was kept low even without such a process of filtration through the hollow fiber filtration membrane (FIG. 4).

From these results, it was shown that, while filtration through a hollow fiber filtration membrane is indispensable in cases where the viral method is used, such filtration is not necessary in cases where the stably expressing cell line method is used.

Example 3: Measurement of Endotoxin Using Endotoxin-Measuring Agent of Present Invention (3-1) Measurement Using Endotoxin-Measuring Agent 1

To the endotoxin-measuring agent 1 (freeze-dried product), 3.3 mL of 100 mM Tris buffer (pH 8.0) was added, to dissolve the agent. In this solution, the protein concentration of each of the culture supernatants containing the factor C, factor B, and proclotting enzyme was about 60 μg/mL.

Into each well of a 96-well microtiter plate, 50 μL of an endotoxin solution at a concentration of 0, 0.001, 0.01, or 0.1 EU/mL was aliquoted, and 50 μL of the endotoxin-measuring agent solution prepared by dissolving the agent was added to the each well, followed by mixing the resulting mixture. The mixture was then incubated at 37° C. for 30 minutes, and the endotoxin concentration was measured according to the reaction rate method in which the absorbance at 405 nm was measured with time during the incubation. In this reaction solution, the protein concentration of each of the culture supernatants containing the factor C, factor B, and proclotting enzyme was about 30 μg/mL.

The results are shown in FIG. 8. As a result, it was shown that, in cases where the factors expressed by the viral method are used, the absorbance change rate linearly increases within the range of 0.001 to 0.10 EU/mL as the concentration of endotoxin increases.

(3-2) Measurement Using Endotoxin-Measuring Agent 2

To the endotoxin-measuring agent 2 (freeze-dried product), 3.3 mL of 100 mM Hepes buffer (pH 7.6) was added, to dissolve the agent. In this solution, the protein concentration of each of the culture supernatants containing the factor C, factor B, and proclotting enzyme was about 60 μg/mL.

Into each well of a 96-well microtiter plate, 50 μL of an endotoxin solution at a concentration of 0, 0.0005, 0.001, 0.005, 0.01, or 0.1 EU/mL was aliquoted, and 50 μL of the endotoxin-measuring agent solution prepared by dissolving the agent was added to the each well, followed by mixing the resulting mixture. The mixture was then incubated at 37° C. for 30 minutes, and the endotoxin concentration was measured according to the reaction rate method in which the absorbance at 405 nm was measured with time during the incubation. In this reaction solution, the protein concentration of each of the culture supernatants containing the factor C, factor B, and proclotting enzyme was about 30 μg/mL.

The results are shown in FIG. 9. As a result, it was shown that, in cases where the factors expressed by the stably expressing cell method are used, the absorbance change rate linearly increases within the range of 0.0005 to 0.1 EU/mL as the concentration of endotoxin increases.

Based on the above results, with either of the endotoxin-measuring agents, quantification of endotoxin at a concentration of 0.001 EU/mL was possible within 30 minutes. Further, with the endotoxin-measuring agent 2, endotoxin at a concentration of 0.0005 EU/mL was able to be measured within 30 minutes. Thus, it was shown that the endotoxin-measuring agents of the present invention enable more rapid and sensitive quantification of endotoxin compared to the conventional methods (by which the measurement takes not less than 1 hour, and the detection sensitivity of 0.001 EU/mL has not been achieved). Further, it was shown that, in either case, the expressed factors can be used for a measuring agent as they are without purification.

Example 4: Difference in Activity Between Recombinant Factor C Protein and Naturally Occurring Factor C Protein (4-1) Purification of Recombinant Factor C Protein and Naturally Occurring Factor C Protein By covalently bonding 2 mg of the anti-factor C antibody (2C12, which is the same as the one used above) to sepharose column 1 ml (GE Healthcare), 2 factor-C antibody columns were prepared. The preparation was carried out according to the method described in the attached instructions. To 76 mL of culture supernatant containing recombinant factor C protein derived by the stably expressing cell method that was prepared by the same process as described in the above “(1-2-2) Recovery of Recombinant Protein”, an equal amount of 20 mM Tris-HCl buffer (pH 8.0) containing 2 M sodium chloride and 2 mM EDTA was added to dilute the culture supernatant, followed by subjecting the resulting dilution to one of the factor-C antibody columns. Similarly, to 76 mL of an extract of horseshoe crab blood cells, an equal amount of 20 mM Tris-HCl buffer (pH 8.0) containing 2 M sodium chloride and 2 mM EDTA was added to dilute the extract, followed by subjecting the resulting dilution to the other of the factor-C antibody columns. The both columns were washed sequentially with 20 mL each of 20 mM Tris-HCl buffer (pH 8.0) containing 200 mM or 450 mM sodium chloride, and elution was then carried out with 50 mM glycine buffer (pH 2.5). Into a 1.5 mL tube in which 0.025 mL of 1M Trizma base (Sigma) was preliminarily placed, 1 mL of each eluted fraction was collected, to return the pH of the eluted solution to neutral.

(4-2) Comparison of Concentration Between Purified Recombinant and Naturally Occurring Factor C Proteins The eluted fractions of the purified recombinant and naturally occurring factor C proteins were subjected to separation by 5-20% polyacrylamide gel electrophoresis (under non-reducing conditions) in the presence of SDS. In this process, purified bovine serum albumin (=BSA) whose concentration is known was also subjected to separation on the same gel as samples for concentration reference (FIG. 10). The intensities of BSA bands on the gel stained with Coomassie brilliant blue were quantified with a densitometer, and plotted against the concentrations of the BSA protein, to prepare a calibration curve (FIG. 11). Based on the band intensities of the purified factor C proteins and the calibration curve, the concentrations of the purified factor C proteins were approximated. As a result, it was revealed that, as for the purified samples, the naturally occurring factor C protein had about 4 times the concentration of the recombinant factor C protein.

(4-3) Comparison of Activity Between Purified Recombinant and Naturally Occurring Factor C Proteins A comparison of the activity was made using the purified recombinant and naturally occurring factor C proteins. In this comparison, the protein concentration was equalized between the purified factor Cs based on the results of (4-2). Into each well of a 96-well microtiter plate, 50 μL of an endotoxin solution at a concentration of 0, 0.05, 0.1, or 0.5 EU/mL was aliquoted. Reagents and culture supernatants were added to the each well such that 50 mM Tris buffer (pH 8.0), 0.2 μg/mL purified factor C protein, μg/mL protein of each of culture supernatants containing the recombinant factor B and recombinant proclotting enzyme, and 0.3 mM of the synthetic substrate Boc-Leu-Gly-Arg-pNA were contained in the reaction solution, whose total volume was adjusted to 100 μL by addition of water for injection. The reaction solution was incubated at 37° C. for 30 minutes, and the analysis was carried out according to the reaction rate method in which the absorbance at 405 nm was measured with time during the incubation.

As a result, it was revealed that the purified recombinant factor C protein had about twice the activity of the purified naturally occurring factor C protein (FIG. 12). The above results suggest that the recombinant factor C has a higher specific activity than the naturally occurring factor C.

INDUSTRIAL APPLICABILITY

By the present invention, endotoxin can be rapidly and highly sensitively measured. Further, by the present invention, an endotoxin-measuring agent can be simply and rapidly produced at a low cost. Therefore, the present invention can be extremely effectively used for detection of endotoxin.

DESCRIPTION OF SEQUENCE LISTING

SEQ ID NO:1 DNA sequence of factor C gene of Japanese horseshoe crab

SEQ ID NO:2 Amino acid sequence of factor C of Japanese horseshoe crab

SEQ ID NO:3 DNA sequence of factor B gene of Japanese horseshoe crab

SEQ ID NO:4 Amino acid sequence of factor B of Japanese horseshoe crab

SEQ ID NO:5 DNA sequence of proclotting enzyme gene of Japanese horseshoe crab

SEQ ID NO:6 Amino acid sequence of proclotting enzyme of Japanese horseshoe crab SEQ ID NO:7 DNA sequence of His-tag-attached factor C gene SEQ ID NO:8 DNA sequence of factor B gene whose codons are optimized for expression in insect cells SEQ ID NO:9 DNA sequence of proclotting enzyme gene whose codons are optimized for expression in insect cells SEQ ID NO:10 Primer for preparation of His-tag-free factor C gene SEQ ID NO:11 Primer for preparation of His-tag-free factor C gene SEQ ID NO:12 Peptide sequence

What is claimed is:

1. A method for producing an endotoxin measuring agent, the method comprising:
   - (A) incorporating each of the DNAs (1) to (3) below into a baculovirus:
     - (1) a DNA encoding a factor C, wherein the factor C is a protein described as (A') or (B') below, and does not have His-tag sequence or any peptide attached at the C-terminus:
       - (A') a protein consisting of the amino acid sequence shown in SEQ ID NO: 2;
       - (B') a protein consisting of an amino acid sequence having not less than 90% sequence identity compared to the full-length amino acid sequence shown in SEQ ID NO:2, wherein the protein has factor C activity;
     - (2) a DNA encoding a factor B of a horseshoe crab; and
     - (3) a DNA encoding a proclotting enzyme of a horseshoe crab;
   - (B) infecting insect cells with the baculovirus;
   - (C) allowing the insect cells infected with the baculovirus to express the factor C, the factor B and the proclotting enzyme;
   - (D) recovering factor C, factor B, and proclotting enzyme, which are expressed from the insect cells into a culture supernatant;
   - (E) eliminating the baculovirus from the expressed factor C, the expressed factor B, and the expressed proclotting enzyme; and
   - (F) formulating the endotoxin measuring agent comprising the expressed factor C, the expressed factor B, and the expressed proclotting enzyme from which the baculovirus was eliminated.

2. The method according to claim 1, wherein said insect cell is at least one selected from the group consisting of Sf9, Sf21, and SF+.

3. The method according to claim 1, wherein the endotoxin measuring agent has a detection sensitivity of 0.005 EU/mL.

4. The method according to claim 1, the concentrations of the factor C in the endotoxin measuring agent before contacting with a test sample is 20 to 100 μg/mL.

5. The method according to claim 1, wherein the endotoxin measuring agent further comprises a substrate for detection.

6. The method according to claim 5, wherein the substrate for detection is a synthetic substrate represented by the general formula X—Y—Z, wherein X represents a protecting group, Y represents a peptide, and Z represents a dye bound to Y via an amide bond.

7. The method according to claim 6, wherein the dye is a para-nitroaniline.

8. The method according to claim 1, wherein the factor C, the factor B and the proclotting enzyme are separately expressed in the insect cells constructed for expressing respective factors.

* * * * *

SEQUENCE LISTING

```
<160> NUMBER OF SEQ ID NOS: 12

<210> SEQ ID NO 1
<211> LENGTH: 3060
<212> TYPE: DNA
<213> ORGANISM: Tachypleus tridentatus
<220> FEATURE:
<221> NAME/KEY: CDS
<222> LOCATION: (1)..(3060)

<400> SEQUENCE: 1

atg gtc tta gcg tcg ttt ttg gtg tct ggt tta gtt cta ggg ata cta       48
Met Val Leu Ala Ser Phe Leu Val Ser Gly Leu Val Leu Gly Ile Leu
1               5                   10                  15

gcc caa caa atg cgt cca gtt cag tcc aga gga gta gat ctg ggc ttg       96
Ala Gln Gln Met Arg Pro Val Gln Ser Arg Gly Val Asp Leu Gly Leu
            20                  25                  30

tgt gat gaa acg agg ttc gag tgt aag tgt gga gat cca ggc tat gtg      144
Cys Asp Glu Thr Arg Phe Glu Cys Lys Cys Gly Asp Pro Gly Tyr Val
```

-continued

```
        35                  40                  45

ttc aac gtc cct atg aaa caa tgc acg tac ttc tat cga tgg agg cct      192
Phe Asn Val Pro Met Lys Gln Cys Thr Tyr Phe Tyr Arg Trp Arg Pro
    50                  55                  60

tat tgt aaa cca tgt gat gac ctg gag gct aag gac att tgt cca aag      240
Tyr Cys Lys Pro Cys Asp Asp Leu Glu Ala Lys Asp Ile Cys Pro Lys
65                  70                  75                  80

tac aaa cga tgt caa gag tgt aag gct ggt ctt gat agt tgt gtt act      288
Tyr Lys Arg Cys Gln Glu Cys Lys Ala Gly Leu Asp Ser Cys Val Thr
                85                  90                  95

tgt cca cct aac aaa tat ggt act tgg tgt agc ggt gaa tgt caa tgt      336
Cys Pro Pro Asn Lys Tyr Gly Thr Trp Cys Ser Gly Glu Cys Gln Cys
            100                 105                 110

aag aat gga ggt atc tgt gac cag agg aca gga gct tgt acc tgt cgt      384
Lys Asn Gly Gly Ile Cys Asp Gln Arg Thr Gly Ala Cys Thr Cys Arg
        115                 120                 125

gac aga tat gaa gga gcg cac tgt gaa att ctc aaa ggt tgt cct ctt      432
Asp Arg Tyr Glu Gly Ala His Cys Glu Ile Leu Lys Gly Cys Pro Leu
    130                 135                 140

ctt cca tcg gat tct caa gtt cag gaa gtc aga aac cca cca gat aat      480
Leu Pro Ser Asp Ser Gln Val Gln Glu Val Arg Asn Pro Pro Asp Asn
145                 150                 155                 160

ccc caa act att gac tac agc tgt tca cca ggg ttc aag ctt aaa ggc      528
Pro Gln Thr Ile Asp Tyr Ser Cys Ser Pro Gly Phe Lys Leu Lys Gly
                165                 170                 175

gtg gca cga att agc tgt ctc cca aat gga cag tgg agt agc ttt cca      576
Val Ala Arg Ile Ser Cys Leu Pro Asn Gly Gln Trp Ser Ser Phe Pro
            180                 185                 190

ccc aaa tgt att cga gaa tgt gcc aag gtt tca tct cca gaa cac ggg      624
Pro Lys Cys Ile Arg Glu Cys Ala Lys Val Ser Ser Pro Glu His Gly
        195                 200                 205

aaa gtg aat gct cct agt ggc aat atg ata gaa ggg gct act tta cgg      672
Lys Val Asn Ala Pro Ser Gly Asn Met Ile Glu Gly Ala Thr Leu Arg
    210                 215                 220

ttc tca tgt gat agt ccc tac tac ttg att ggt caa gaa aca tta acc      720
Phe Ser Cys Asp Ser Pro Tyr Tyr Leu Ile Gly Gln Glu Thr Leu Thr
225                 230                 235                 240

tgc cag ggt aat ggt cag tgg agt gga caa ata cca caa tgt aag aag      768
Cys Gln Gly Asn Gly Gln Trp Ser Gly Gln Ile Pro Gln Cys Lys Lys
                245                 250                 255

ttg gtc ttc tgt cct gac ctt gat cct gta aac cat gct gaa cac cag      816
Leu Val Phe Cys Pro Asp Leu Asp Pro Val Asn His Ala Glu His Gln
            260                 265                 270

gtt aaa att ggt gtg gaa caa aaa tat ggt cag ttt cct caa ggc act      864
Val Lys Ile Gly Val Glu Gln Lys Tyr Gly Gln Phe Pro Gln Gly Thr
        275                 280                 285

gaa gtg acc tat acg tgt tcg ggt aac tac ttc ttg atg ggt ttt aac      912
Glu Val Thr Tyr Thr Cys Ser Gly Asn Tyr Phe Leu Met Gly Phe Asn
    290                 295                 300

acc tta aaa tgt aac cct gat ggg tcc tgg tca gga tca cag cca tcc      960
Thr Leu Lys Cys Asn Pro Asp Gly Ser Trp Ser Gly Ser Gln Pro Ser
305                 310                 315                 320

tgt gtt aaa gtg gca gac aga gag gtc gac tgt gac agt aaa gct gta     1008
Cys Val Lys Val Ala Asp Arg Glu Val Asp Cys Asp Ser Lys Ala Val
                325                 330                 335

gac ttc ttg gat gat gtt ggt gaa cct gtc agg atc cac tgt cct gct     1056
Asp Phe Leu Asp Asp Val Gly Glu Pro Val Arg Ile His Cys Pro Ala
            340                 345                 350

ggc tgt tct ttg aca gct ggt act gtg tgg ggt aca gcc ata tac cac     1104
```

-continued

```
Gly Cys Ser Leu Thr Ala Gly Thr Val Trp Gly Thr Ala Ile Tyr His
        355                 360                 365

gaa ctt tcc tca gtg tgt cgt gca gcc atc cat gct ggc aag ctt cca      1152
Glu Leu Ser Ser Val Cys Arg Ala Ala Ile His Ala Gly Lys Leu Pro
    370                 375                 380

aac tct gga ggg gcg gtg cat gta gtg aac aat ggc ccc tac tcg gac      1200
Asn Ser Gly Gly Ala Val His Val Val Asn Asn Gly Pro Tyr Ser Asp
385                 390                 395                 400

ttt ctg ggt agt gac ctg aat ggg ata aaa tcg gaa gag ttg aag tct      1248
Phe Leu Gly Ser Asp Leu Asn Gly Ile Lys Ser Glu Glu Leu Lys Ser
                405                 410                 415

ctt gcc cgc agt ttt cga ttt gat tat gtc agt tca tcc aca gca ggt      1296
Leu Ala Arg Ser Phe Arg Phe Asp Tyr Val Ser Ser Ser Thr Ala Gly
            420                 425                 430

aga tca gga tgt cct gat gga tgg ttt gag gta gaa gag aac tgt gtg      1344
Arg Ser Gly Cys Pro Asp Gly Trp Phe Glu Val Glu Glu Asn Cys Val
        435                 440                 445

tac gtt aca tca aaa cag aga gcc tgg gaa aga gct caa ggt gtg tgt      1392
Tyr Val Thr Ser Lys Gln Arg Ala Trp Glu Arg Ala Gln Gly Val Cys
    450                 455                 460

acc aat atg gct gct cgt ctt gct gtg cta gac aaa gat cta att ccg      1440
Thr Asn Met Ala Ala Arg Leu Ala Val Leu Asp Lys Asp Leu Ile Pro
465                 470                 475                 480

agt tcc ttg act gag act cta cga ggg aaa ggg tta aca acc aca tgg      1488
Ser Ser Leu Thr Glu Thr Leu Arg Gly Lys Gly Leu Thr Thr Thr Trp
                485                 490                 495

ata gga ttg cac aga cta gat gct gag aag ccc ttt gtt tgg gag cta      1536
Ile Gly Leu His Arg Leu Asp Ala Glu Lys Pro Phe Val Trp Glu Leu
            500                 505                 510

atg gat cgt agt aat gtg gtt ctg aat gat aac cta aca ttc tgg gcc      1584
Met Asp Arg Ser Asn Val Val Leu Asn Asp Asn Leu Thr Phe Trp Ala
        515                 520                 525

tct ggc gaa cct gga aat gaa act aac tgt gta tat ctg gac atc cga      1632
Ser Gly Glu Pro Gly Asn Glu Thr Asn Cys Val Tyr Leu Asp Ile Arg
    530                 535                 540

gat cag ctg cag cct gtg tgg aaa acc aag tca tgt ttt cag ccc tca      1680
Asp Gln Leu Gln Pro Val Trp Lys Thr Lys Ser Cys Phe Gln Pro Ser
545                 550                 555                 560

agc ttt gct tgc atg atg gat ttg tca gac aga aat aaa gcc aaa tgc      1728
Ser Phe Ala Cys Met Met Asp Leu Ser Asp Arg Asn Lys Ala Lys Cys
                565                 570                 575

gat gac cct gga cca ctg gaa aat gga cac gcc aca ctt cat gga caa      1776
Asp Asp Pro Gly Pro Leu Glu Asn Gly His Ala Thr Leu His Gly Gln
            580                 585                 590

agt att gat ggg ttc tat gct ggt tct tct ata agg tac agc tgt gag      1824
Ser Ile Asp Gly Phe Tyr Ala Gly Ser Ser Ile Arg Tyr Ser Cys Glu
        595                 600                 605

gtt ctc cac tac ctc agt gga act gag acc gta act tgt aca aca aat      1872
Val Leu His Tyr Leu Ser Gly Thr Glu Thr Val Thr Cys Thr Thr Asn
    610                 615                 620

ggc aca tgg agt gct cct aaa cct cga tgt atc aaa gtc atc acc tgc      1920
Gly Thr Trp Ser Ala Pro Lys Pro Arg Cys Ile Lys Val Ile Thr Cys
625                 630                 635                 640

caa aac cct cct gta cca tca tat ggt tct gtg gaa atc aaa ccc cca      1968
Gln Asn Pro Pro Val Pro Ser Tyr Gly Ser Val Glu Ile Lys Pro Pro
                645                 650                 655

agt cgg aca aac tcg atc agt cgt gtt ggg tca cct ttc ttg agg ttg      2016
Ser Arg Thr Asn Ser Ile Ser Arg Val Gly Ser Pro Phe Leu Arg Leu
            660                 665                 670
```

```
cca cgg tta ccc ctc cca tta gcc aga gca gcc aaa cct cct cca aaa      2064
Pro Arg Leu Pro Leu Pro Leu Ala Arg Ala Ala Lys Pro Pro Pro Lys
        675                 680                 685

cct aga tcc tca caa ccc tct act gtg gac ttg gct tct aaa gtt aaa      2112
Pro Arg Ser Ser Gln Pro Ser Thr Val Asp Leu Ala Ser Lys Val Lys
    690                 695                 700

cta cct gaa ggt cat tac cgg gta ggg tct cga gcc att tac acg tgc      2160
Leu Pro Glu Gly His Tyr Arg Val Gly Ser Arg Ala Ile Tyr Thr Cys
705                 710                 715                 720

gag tcg aga tac tac gaa cta ctt gga tct caa ggc aga aga tgt gac      2208
Glu Ser Arg Tyr Tyr Glu Leu Leu Gly Ser Gln Gly Arg Arg Cys Asp
                725                 730                 735

tct aat gga aac tgg agt ggt cgg ccc gct agc tgt att cca gtt tgt      2256
Ser Asn Gly Asn Trp Ser Gly Arg Pro Ala Ser Cys Ile Pro Val Cys
            740                 745                 750

gga cgg tca gac tct cct cgt tct cct ttc atc tgg aat ggg aat tct      2304
Gly Arg Ser Asp Ser Pro Arg Ser Pro Phe Ile Trp Asn Gly Asn Ser
        755                 760                 765

aca gaa ata ggt cag tgg ccg tgg cag gca gga atc tct cga tgg ctt      2352
Thr Glu Ile Gly Gln Trp Pro Trp Gln Ala Gly Ile Ser Arg Trp Leu
    770                 775                 780

gca gac cac aat atg tgg ttt ctc cag tgt gga gga tcc cta ttg aat      2400
Ala Asp His Asn Met Trp Phe Leu Gln Cys Gly Gly Ser Leu Leu Asn
785                 790                 795                 800

gag aaa tgg atc gtc act gct gcc cac tgt gtc acc tac tct gct act      2448
Glu Lys Trp Ile Val Thr Ala Ala His Cys Val Thr Tyr Ser Ala Thr
                805                 810                 815

gct gag ata att gat ccc agt cag ttt aaa atc tat ctg ggc aag tac      2496
Ala Glu Ile Ile Asp Pro Ser Gln Phe Lys Ile Tyr Leu Gly Lys Tyr
            820                 825                 830

tac cgt gat gac agt aga gac gat gac tac gta caa gta aga gag gct      2544
Tyr Arg Asp Asp Ser Arg Asp Asp Asp Tyr Val Gln Val Arg Glu Ala
        835                 840                 845

ctc gag atc cac gta aat cct aac tac gac ccc ggc aat ctc aac ttt      2592
Leu Glu Ile His Val Asn Pro Asn Tyr Asp Pro Gly Asn Leu Asn Phe
    850                 855                 860

gac ata gcc cta att caa ctg aaa act cct gtt act ttg aca aca cga      2640
Asp Ile Ala Leu Ile Gln Leu Lys Thr Pro Val Thr Leu Thr Thr Arg
865                 870                 875                 880

gtc caa cca atc tgt ctg cct act gac atc aca aca aga gaa cac ttg      2688
Val Gln Pro Ile Cys Leu Pro Thr Asp Ile Thr Thr Arg Glu His Leu
                885                 890                 895

aag gag gga aca tta gca gtg gtg aca ggt tgg ggt ttg aat gaa aac      2736
Lys Glu Gly Thr Leu Ala Val Val Thr Gly Trp Gly Leu Asn Glu Asn
            900                 905                 910

aac aca tat tca gag atg att caa caa gct gtg cta cct gtt gtt gca      2784
Asn Thr Tyr Ser Glu Met Ile Gln Gln Ala Val Leu Pro Val Val Ala
        915                 920                 925

gca agc acc tgt gaa gag ggg tac aag gaa gca gac tta cca ctg aca      2832
Ala Ser Thr Cys Glu Glu Gly Tyr Lys Glu Ala Asp Leu Pro Leu Thr
    930                 935                 940

gta aca gag aac atg ttc tgt gca ggt tac aag aag gga cgt tat gat      2880
Val Thr Glu Asn Met Phe Cys Ala Gly Tyr Lys Lys Gly Arg Tyr Asp
945                 950                 955                 960

gcc tgc agt ggg gac agt gga gga cca tta gtg ttt gct gat gat tcc      2928
Ala Cys Ser Gly Asp Ser Gly Gly Pro Leu Val Phe Ala Asp Asp Ser
                965                 970                 975

cgt acc gaa agg cgg tgg gtc ttg gaa ggg att gtc agc tgg ggc agt      2976
Arg Thr Glu Arg Arg Trp Val Leu Glu Gly Ile Val Ser Trp Gly Ser
            980                 985                 990
```

ccc agt gga tgt ggc aag gct aac cag tat ggg ggc ttc act aaa gtt 3024
Pro Ser Gly Cys Gly Lys Ala Asn Gln Tyr Gly Gly Phe Thr Lys Val
995 1000 1005 aac gtt ttt cta tca tgg att agg cag ttc att tga 3060
Asn Val Phe Leu Ser Trp Ile Arg Gln Phe Ile
1010 1015

<210> SEQ ID NO 2
<211> LENGTH: 1019
<212> TYPE: PRT
<213> ORGANISM: Tachypleus tridentatus

<400> SEQUENCE: 2

Met Val Leu Ala Ser Phe Leu Val Ser Gly Leu Val Leu Gly Ile Leu
1 5 10 15

Ala Gln Gln Met Arg Pro Val Gln Ser Arg Gly Val Asp Leu Gly Leu
20 25 30

Cys Asp Glu Thr Arg Phe Glu Cys Lys Cys Gly Asp Pro Gly Tyr Val
35 40 45

Phe Asn Val Pro Met Lys Gln Cys Thr Tyr Phe Tyr Arg Trp Arg Pro
50 55 60

Tyr Cys Lys Pro Cys Asp Asp Leu Glu Ala Lys Asp Ile Cys Pro Lys
65 70 75 80

Tyr Lys Arg Cys Gln Glu Cys Lys Ala Gly Leu Asp Ser Cys Val Thr
85 90 95

Cys Pro Pro Asn Lys Tyr Gly Thr Trp Cys Ser Gly Glu Cys Gln Cys
100 105 110

Lys Asn Gly Gly Ile Cys Asp Gln Arg Thr Gly Ala Cys Thr Cys Arg
115 120 125

Asp Arg Tyr Glu Gly Ala His Cys Glu Ile Leu Lys Gly Cys Pro Leu
130 135 140

Leu Pro Ser Asp Ser Gln Val Gln Glu Val Arg Asn Pro Pro Asp Asn
145 150 155 160

Pro Gln Thr Ile Asp Tyr Ser Cys Ser Pro Gly Phe Lys Leu Lys Gly
165 170 175

Val Ala Arg Ile Ser Cys Leu Pro Asn Gly Gln Trp Ser Ser Phe Pro
180 185 190

Pro Lys Cys Ile Arg Glu Cys Ala Lys Val Ser Ser Pro Glu His Gly
195 200 205

Lys Val Asn Ala Pro Ser Gly Asn Met Ile Glu Gly Ala Thr Leu Arg
210 215 220

Phe Ser Cys Asp Ser Pro Tyr Tyr Leu Ile Gly Gln Glu Thr Leu Thr
225 230 235 240

Cys Gln Gly Asn Gly Gln Trp Ser Gly Gln Ile Pro Gln Cys Lys Lys
245 250 255

Leu Val Phe Cys Pro Asp Leu Asp Pro Val Asn His Ala Glu His Gln
260 265 270

Val Lys Ile Gly Val Glu Gln Lys Tyr Gly Gln Phe Pro Gln Gly Thr
275 280 285

Glu Val Thr Tyr Thr Cys Ser Gly Asn Tyr Phe Leu Met Gly Phe Asn
290 295 300

Thr Leu Lys Cys Asn Pro Asp Gly Ser Trp Ser Gly Ser Gln Pro Ser
305 310 315 320

Cys Val Lys Val Ala Asp Arg Glu Val Asp Cys Asp Ser Lys Ala Val
325 330 335

```
Asp Phe Leu Asp Asp Val Gly Glu Pro Val Arg Ile His Cys Pro Ala
            340                 345                 350

Gly Cys Ser Leu Thr Ala Gly Thr Val Trp Gly Thr Ala Ile Tyr His
        355                 360                 365

Glu Leu Ser Ser Val Cys Arg Ala Ala Ile His Ala Gly Lys Leu Pro
    370                 375                 380

Asn Ser Gly Gly Ala Val His Val Val Asn Asn Gly Pro Tyr Ser Asp
385                 390                 395                 400

Phe Leu Gly Ser Asp Leu Asn Gly Ile Lys Ser Glu Glu Leu Lys Ser
                405                 410                 415

Leu Ala Arg Ser Phe Arg Phe Asp Tyr Val Ser Ser Ser Thr Ala Gly
            420                 425                 430

Arg Ser Gly Cys Pro Asp Gly Trp Phe Glu Val Glu Glu Asn Cys Val
        435                 440                 445

Tyr Val Thr Ser Lys Gln Arg Ala Trp Glu Arg Ala Gln Gly Val Cys
    450                 455                 460

Thr Asn Met Ala Ala Arg Leu Ala Val Leu Asp Lys Asp Leu Ile Pro
465                 470                 475                 480

Ser Ser Leu Thr Glu Thr Leu Arg Gly Lys Gly Leu Thr Thr Thr Trp
                485                 490                 495

Ile Gly Leu His Arg Leu Asp Ala Glu Lys Pro Phe Val Trp Glu Leu
            500                 505                 510

Met Asp Arg Ser Asn Val Val Leu Asn Asp Asn Leu Thr Phe Trp Ala
        515                 520                 525

Ser Gly Glu Pro Gly Asn Glu Thr Asn Cys Val Tyr Leu Asp Ile Arg
    530                 535                 540

Asp Gln Leu Gln Pro Val Trp Lys Thr Lys Ser Cys Phe Gln Pro Ser
545                 550                 555                 560

Ser Phe Ala Cys Met Met Asp Leu Ser Asp Arg Asn Lys Ala Lys Cys
                565                 570                 575

Asp Asp Pro Gly Pro Leu Glu Asn Gly His Ala Thr Leu His Gly Gln
            580                 585                 590

Ser Ile Asp Gly Phe Tyr Ala Gly Ser Ser Ile Arg Tyr Ser Cys Glu
        595                 600                 605

Val Leu His Tyr Leu Ser Gly Thr Glu Thr Val Thr Cys Thr Thr Asn
    610                 615                 620

Gly Thr Trp Ser Ala Pro Lys Pro Arg Cys Ile Lys Val Ile Thr Cys
625                 630                 635                 640

Gln Asn Pro Pro Val Pro Ser Tyr Gly Ser Val Glu Ile Lys Pro Pro
                645                 650                 655

Ser Arg Thr Asn Ser Ile Ser Arg Val Gly Ser Pro Phe Leu Arg Leu
            660                 665                 670

Pro Arg Leu Pro Leu Pro Leu Ala Arg Ala Ala Lys Pro Pro Pro Lys
        675                 680                 685

Pro Arg Ser Ser Gln Pro Ser Thr Val Asp Leu Ala Ser Lys Val Lys
    690                 695                 700

Leu Pro Glu Gly His Tyr Arg Val Gly Ser Arg Ala Ile Tyr Thr Cys
705                 710                 715                 720

Glu Ser Arg Tyr Tyr Glu Leu Leu Gly Ser Gln Gly Arg Arg Cys Asp
                725                 730                 735

Ser Asn Gly Asn Trp Ser Gly Arg Pro Ala Ser Cys Ile Pro Val Cys
            740                 745                 750
```

```
Gly Arg Ser Asp Ser Pro Arg Ser Pro Phe Ile Trp Asn Gly Asn Ser
        755                 760                 765

Thr Glu Ile Gly Gln Trp Pro Trp Gln Ala Gly Ile Ser Arg Trp Leu
    770                 775                 780

Ala Asp His Asn Met Trp Phe Leu Gln Cys Gly Gly Ser Leu Leu Asn
785                 790                 795                 800

Glu Lys Trp Ile Val Thr Ala Ala His Cys Val Thr Tyr Ser Ala Thr
                805                 810                 815

Ala Glu Ile Ile Asp Pro Ser Gln Phe Lys Ile Tyr Leu Gly Lys Tyr
            820                 825                 830

Tyr Arg Asp Asp Ser Arg Asp Asp Asp Tyr Val Gln Val Arg Glu Ala
        835                 840                 845

Leu Glu Ile His Val Asn Pro Asn Tyr Asp Pro Gly Asn Leu Asn Phe
    850                 855                 860

Asp Ile Ala Leu Ile Gln Leu Lys Thr Pro Val Thr Leu Thr Thr Arg
865                 870                 875                 880

Val Gln Pro Ile Cys Leu Pro Thr Asp Ile Thr Thr Arg Glu His Leu
                885                 890                 895

Lys Glu Gly Thr Leu Ala Val Val Thr Gly Trp Gly Leu Asn Glu Asn
            900                 905                 910

Asn Thr Tyr Ser Glu Met Ile Gln Gln Ala Val Leu Pro Val Val Ala
        915                 920                 925

Ala Ser Thr Cys Glu Glu Gly Tyr Lys Glu Ala Asp Leu Pro Leu Thr
    930                 935                 940

Val Thr Glu Asn Met Phe Cys Ala Gly Tyr Lys Lys Gly Arg Tyr Asp
945                 950                 955                 960

Ala Cys Ser Gly Asp Ser Gly Gly Pro Leu Val Phe Ala Asp Asp Ser
                965                 970                 975

Arg Thr Glu Arg Arg Trp Val Leu Glu Gly Ile Val Ser Trp Gly Ser
            980                 985                 990

Pro Ser Gly Cys Gly Lys Ala Asn  Gln Tyr Gly Gly Phe  Thr Lys Val
        995                 1000                1005

Asn Val  Phe Leu Ser Trp Ile  Arg Gln Phe Ile
    1010                1015


<210> SEQ ID NO 3
<211> LENGTH: 1203
<212> TYPE: DNA
<213> ORGANISM: Tachypleus tridentatus
<220> FEATURE:
<221> NAME/KEY: CDS
<222> LOCATION: (1)..(1203)

<400> SEQUENCE: 3

atg acg tgg ata tgt gtg ata acg ttg ttt gct ctg gct tct gct acg       48
Met Thr Trp Ile Cys Val Ile Thr Leu Phe Ala Leu Ala Ser Ala Thr
1               5                   10                  15

ttg ggt aac aaa gtt agt aga gtg ggg gtc ctc ttc ccc aag aca cgg       96
Leu Gly Asn Lys Val Ser Arg Val Gly Val Leu Phe Pro Lys Thr Arg
            20                  25                  30

aac gac aat gag tgt aca gca aga ggg gga ttg aaa gga tcc tgc aaa      144
Asn Asp Asn Glu Cys Thr Ala Arg Gly Gly Leu Lys Gly Ser Cys Lys
        35                  40                  45

tcc ctc ata gac tgt cct agt gtc ttg gct acg ttg aag gac agt ttt      192
Ser Leu Ile Asp Cys Pro Ser Val Leu Ala Thr Leu Lys Asp Ser Phe
    50                  55                  60

cct gtc gtt tgc tct tgg aat ggt cga ttt cag cct att gtc tgc tgt      240
```

-continued

```
Pro Val Val Cys Ser Trp Asn Gly Arg Phe Gln Pro Ile Val Cys Cys
65                  70                  75                  80

cct gat gca ata gca cca cca cct gta acc aca aca gct gta act gta      288
Pro Asp Ala Ile Ala Pro Pro Pro Val Thr Thr Thr Ala Val Thr Val
                85                  90                  95

ata tct aca aaa gaa cca aag ctt cca aga tta cat ata tca ggt tgt      336
Ile Ser Thr Lys Glu Pro Lys Leu Pro Arg Leu His Ile Ser Gly Cys
            100                 105                 110

gga aaa aga aaa gtc aaa ata gat att aca act gtt gga cgc tct gga      384
Gly Lys Arg Lys Val Lys Ile Asp Ile Thr Thr Val Gly Arg Ser Gly
        115                 120                 125

tca cca ata ctt cct ccg ata tct act cct caa aat tca aca ggt ggg      432
Ser Pro Ile Leu Pro Pro Ile Ser Thr Pro Gln Asn Ser Thr Gly Gly
    130                 135                 140

aga gga att att gct gga ggc gta gaa gcc aaa att ggc gcg tgg cct      480
Arg Gly Ile Ile Ala Gly Gly Val Glu Ala Lys Ile Gly Ala Trp Pro
145                 150                 155                 160

tgg atg gca gct gtt ttt gtg aaa aac ttt ggc att ggc aga ttc cac      528
Trp Met Ala Ala Val Phe Val Lys Asn Phe Gly Ile Gly Arg Phe His
                165                 170                 175

tgt gct ggt agc ata atc agt aac aag tac att ttg tca gct gcc cac      576
Cys Ala Gly Ser Ile Ile Ser Asn Lys Tyr Ile Leu Ser Ala Ala His
            180                 185                 190

gcc ttc ctt atc gga ggt cga aag ttg acc cca act cgc tta gct gtc      624
Ala Phe Leu Ile Gly Gly Arg Lys Leu Thr Pro Thr Arg Leu Ala Val
        195                 200                 205

cgt gtg gga ggc cac tac ata aag agg ggt caa gag tat cca gtg aaa      672
Arg Val Gly Gly His Tyr Ile Lys Arg Gly Gln Glu Tyr Pro Val Lys
    210                 215                 220

gac gtg att atc cat cct cat tat gta gaa aag gag aac tac aat gat      720
Asp Val Ile Ile His Pro His Tyr Val Glu Lys Glu Asn Tyr Asn Asp
225                 230                 235                 240

ata gcc ata atc gag tta aaa gag gaa ctg aac ttt acg gac ttg gtc      768
Ile Ala Ile Ile Glu Leu Lys Glu Glu Leu Asn Phe Thr Asp Leu Val
                245                 250                 255

aat cct ata tgt ctc cct gat cca gag aca gta acg gat cca tta aaa      816
Asn Pro Ile Cys Leu Pro Asp Pro Glu Thr Val Thr Asp Pro Leu Lys
            260                 265                 270

gac aga att gtg act gca gcg gga tgg ggc gat ctg gat ttc tcc ggt      864
Asp Arg Ile Val Thr Ala Ala Gly Trp Gly Asp Leu Asp Phe Ser Gly
        275                 280                 285

cca cgg agc caa gtt cta cgt gag gta agc atc cca gtt gtt cca gtt      912
Pro Arg Ser Gln Val Leu Arg Glu Val Ser Ile Pro Val Val Pro Val
    290                 295                 300

gat aaa tgt gat caa gcc tat gag aaa ctc aac acc cct tca cta aaa      960
Asp Lys Cys Asp Gln Ala Tyr Glu Lys Leu Asn Thr Pro Ser Leu Lys
305                 310                 315                 320

aat ggg ata acg aat aac ttc ctt tgc gct gga ttg gaa gaa gga ggg     1008
Asn Gly Ile Thr Asn Asn Phe Leu Cys Ala Gly Leu Glu Glu Gly Gly
                325                 330                 335

aaa gac gct tgc caa ggc gat tct ggt gga ccg ttg atg cta gtg aac     1056
Lys Asp Ala Cys Gln Gly Asp Ser Gly Gly Pro Leu Met Leu Val Asn
            340                 345                 350

aac act agg tgg ata gta gta gga gtt gtg tcg ttc ggg cac aag tgt     1104
Asn Thr Arg Trp Ile Val Val Gly Val Val Ser Phe Gly His Lys Cys
        355                 360                 365

gcc gag gaa gga tat cct ggt gtg tac tcg cgc gta gcg agt tac cta     1152
Ala Glu Glu Gly Tyr Pro Gly Val Tyr Ser Arg Val Ala Ser Tyr Leu
    370                 375                 380
```

```
gac tgg atc gcg aaa gtt acg aac tcg tta gat cat gcc gtc act aac      1200
Asp Trp Ile Ala Lys Val Thr Asn Ser Leu Asp His Ala Val Thr Asn
385                 390                 395                 400

taa                                                                  1203


<210> SEQ ID NO 4
<211> LENGTH: 400
<212> TYPE: PRT
<213> ORGANISM: Tachypleus tridentatus

<400> SEQUENCE: 4

Met Thr Trp Ile Cys Val Ile Thr Leu Phe Ala Leu Ala Ser Ala Thr
1               5                   10                  15

Leu Gly Asn Lys Val Ser Arg Val Gly Val Leu Phe Pro Lys Thr Arg
            20                  25                  30

Asn Asp Asn Glu Cys Thr Ala Arg Gly Gly Leu Lys Gly Ser Cys Lys
        35                  40                  45

Ser Leu Ile Asp Cys Pro Ser Val Leu Ala Thr Leu Lys Asp Ser Phe
    50                  55                  60

Pro Val Val Cys Ser Trp Asn Gly Arg Phe Gln Pro Ile Val Cys Cys
65                  70                  75                  80

Pro Asp Ala Ile Ala Pro Pro Pro Val Thr Thr Thr Ala Val Thr Val
                85                  90                  95

Ile Ser Thr Lys Glu Pro Lys Leu Pro Arg Leu His Ile Ser Gly Cys
            100                 105                 110

Gly Lys Arg Lys Val Lys Ile Asp Ile Thr Thr Val Gly Arg Ser Gly
        115                 120                 125

Ser Pro Ile Leu Pro Pro Ile Ser Thr Pro Gln Asn Ser Thr Gly Gly
    130                 135                 140

Arg Gly Ile Ile Ala Gly Gly Val Glu Ala Lys Ile Gly Ala Trp Pro
145                 150                 155                 160

Trp Met Ala Ala Val Phe Val Lys Asn Phe Gly Ile Gly Arg Phe His
                165                 170                 175

Cys Ala Gly Ser Ile Ile Ser Asn Lys Tyr Ile Leu Ser Ala Ala His
            180                 185                 190

Ala Phe Leu Ile Gly Gly Arg Lys Leu Thr Pro Thr Arg Leu Ala Val
        195                 200                 205

Arg Val Gly Gly His Tyr Ile Lys Arg Gly Gln Glu Tyr Pro Val Lys
    210                 215                 220

Asp Val Ile Ile His Pro His Tyr Val Glu Lys Glu Asn Tyr Asn Asp
225                 230                 235                 240

Ile Ala Ile Ile Glu Leu Lys Glu Glu Leu Asn Phe Thr Asp Leu Val
                245                 250                 255

Asn Pro Ile Cys Leu Pro Asp Pro Glu Thr Val Thr Asp Pro Leu Lys
            260                 265                 270

Asp Arg Ile Val Thr Ala Ala Gly Trp Gly Asp Leu Asp Phe Ser Gly
        275                 280                 285

Pro Arg Ser Gln Val Leu Arg Glu Val Ser Ile Pro Val Val Pro Val
    290                 295                 300

Asp Lys Cys Asp Gln Ala Tyr Glu Lys Leu Asn Thr Pro Ser Leu Lys
305                 310                 315                 320

Asn Gly Ile Thr Asn Asn Phe Leu Cys Ala Gly Leu Glu Glu Gly Gly
                325                 330                 335

Lys Asp Ala Cys Gln Gly Asp Ser Gly Gly Pro Leu Met Leu Val Asn
            340                 345                 350
```

```
Asn Thr Arg Trp Ile Val Val Gly Val Val Ser Phe Gly His Lys Cys
        355                 360                 365

Ala Glu Glu Gly Tyr Pro Gly Val Tyr Ser Arg Val Ala Ser Tyr Leu
    370                 375                 380

Asp Trp Ile Ala Lys Val Thr Asn Ser Leu Asp His Ala Val Thr Asn
385                 390                 395                 400


<210> SEQ ID NO 5
<211> LENGTH: 1128
<212> TYPE: DNA
<213> ORGANISM: Tachypleus tridentatus
<220> FEATURE:
<221> NAME/KEY: CDS
<222> LOCATION: (1)..(1128)

<400> SEQUENCE: 5

atg ttg gtg aat aac gtg ttt tca cta ctg tgt ttc cca ctc ttg atg        48
Met Leu Val Asn Asn Val Phe Ser Leu Leu Cys Phe Pro Leu Leu Met
1               5                   10                  15

tct gtg gtt aga tgc agt act ctc agc aga cag cgt aga cag ttt gtt        96
Ser Val Val Arg Cys Ser Thr Leu Ser Arg Gln Arg Arg Gln Phe Val
            20                  25                  30

ttc cct gac gag gaa gaa ctt tgc tca aac cga ttt act gaa gaa gga       144
Phe Pro Asp Glu Glu Glu Leu Cys Ser Asn Arg Phe Thr Glu Glu Gly
        35                  40                  45

aca tgc aaa aat gtc ttg gat tgt aga ata ctt tta caa aaa aat gat       192
Thr Cys Lys Asn Val Leu Asp Cys Arg Ile Leu Leu Gln Lys Asn Asp
    50                  55                  60

tat aat tta ctc aaa gaa tca ata tgc ggc ttt gaa ggc ata aca ccc       240
Tyr Asn Leu Leu Lys Glu Ser Ile Cys Gly Phe Glu Gly Ile Thr Pro
65                  70                  75                  80

aaa gtt tgt tgt ccg aaa tca agc cat gta att tca agt aca cag gca       288
Lys Val Cys Cys Pro Lys Ser Ser His Val Ile Ser Ser Thr Gln Ala
                85                  90                  95

cct cca gaa acc act acg act gaa cgc cca cca aaa cag ata cca ccc       336
Pro Pro Glu Thr Thr Thr Thr Glu Arg Pro Pro Lys Gln Ile Pro Pro
            100                 105                 110

aat ctt cat gaa gtg tgt gga att cac aat act aca act acc agg att       384
Asn Leu His Glu Val Cys Gly Ile His Asn Thr Thr Thr Thr Arg Ile
        115                 120                 125

att gga ggt cgg gaa gca cct att gga gcc tgg ccg tgg atg act gct       432
Ile Gly Gly Arg Glu Ala Pro Ile Gly Ala Trp Pro Trp Met Thr Ala
    130                 135                 140

gtc tac ata aaa caa gga gga atc aga agt gtt cag tgt ggt ggc gca       480
Val Tyr Ile Lys Gln Gly Gly Ile Arg Ser Val Gln Cys Gly Gly Ala
145                 150                 155                 160

ctt gtc act aac agg cac gtg att aca gct tcg cac tgt gtt gta aac       528
Leu Val Thr Asn Arg His Val Ile Thr Ala Ser His Cys Val Val Asn
                165                 170                 175

agt gca gga aca gat gtg atg cca gct gat gta ttc tcg gtt cgt ctg       576
Ser Ala Gly Thr Asp Val Met Pro Ala Asp Val Phe Ser Val Arg Leu
            180                 185                 190

ggt gaa cac aat tta tac agt acc gat gac gat tcg aat cca ata gat       624
Gly Glu His Asn Leu Tyr Ser Thr Asp Asp Asp Ser Asn Pro Ile Asp
        195                 200                 205

ttt gca gtt acg tcg gtg aaa cat cac gaa cac ttt gta ctc gcg acg       672
Phe Ala Val Thr Ser Val Lys His His Glu His Phe Val Leu Ala Thr
    210                 215                 220

tat ttg aat gac atc gca att cta acg tta aat gac aca gtt acg ttt       720
Tyr Leu Asn Asp Ile Ala Ile Leu Thr Leu Asn Asp Thr Val Thr Phe
```

```
225                 230                 235                 240

aca gac aga att cga ccc att tgt cta cct tat cgt aag ttg aga tac      768
Thr Asp Arg Ile Arg Pro Ile Cys Leu Pro Tyr Arg Lys Leu Arg Tyr
                245                 250                 255

gat gat cta gca atg aga aaa ccg ttt atc act gga tgg gga aca aca      816
Asp Asp Leu Ala Met Arg Lys Pro Phe Ile Thr Gly Trp Gly Thr Thr
            260                 265                 270

gca ttt aac ggc cca tct agt gca gtg ttg aga gaa gta cag tta cca      864
Ala Phe Asn Gly Pro Ser Ser Ala Val Leu Arg Glu Val Gln Leu Pro
        275                 280                 285

ata tgg gaa cac gag gcc tgt aga cag gcc tac gag aag gat tta aat      912
Ile Trp Glu His Glu Ala Cys Arg Gln Ala Tyr Glu Lys Asp Leu Asn
    290                 295                 300

att aca aac gtg tat atg tgt gct ggc ttt gca gat ggc ggg aag gat      960
Ile Thr Asn Val Tyr Met Cys Ala Gly Phe Ala Asp Gly Gly Lys Asp
305                 310                 315                 320

gct tgc cag ggt gat tct gga ggt cca atg atg ttg cct gtt aaa acc     1008
Ala Cys Gln Gly Asp Ser Gly Gly Pro Met Met Leu Pro Val Lys Thr
                325                 330                 335

gga gag ttt tat ctc att gga att gtg tct ttc gga aag aaa tgc gca     1056
Gly Glu Phe Tyr Leu Ile Gly Ile Val Ser Phe Gly Lys Lys Cys Ala
            340                 345                 350

ttg cct gga ttt cct ggg gtt tac aca aaa gtg aca gag ttt tta gat     1104
Leu Pro Gly Phe Pro Gly Val Tyr Thr Lys Val Thr Glu Phe Leu Asp
        355                 360                 365

tgg att gca gaa cat atg gtg tag                                     1128
Trp Ile Ala Glu His Met Val
    370                 375


<210> SEQ ID NO 6
<211> LENGTH: 375
<212> TYPE: PRT
<213> ORGANISM: Tachypleus tridentatus

<400> SEQUENCE: 6

Met Leu Val Asn Asn Val Phe Ser Leu Leu Cys Phe Pro Leu Leu Met
1               5                   10                  15

Ser Val Val Arg Cys Ser Thr Leu Ser Arg Gln Arg Arg Gln Phe Val
            20                  25                  30

Phe Pro Asp Glu Glu Glu Leu Cys Ser Asn Arg Phe Thr Glu Glu Gly
        35                  40                  45

Thr Cys Lys Asn Val Leu Asp Cys Arg Ile Leu Leu Gln Lys Asn Asp
    50                  55                  60

Tyr Asn Leu Leu Lys Glu Ser Ile Cys Gly Phe Glu Gly Ile Thr Pro
65                  70                  75                  80

Lys Val Cys Cys Pro Lys Ser Ser His Val Ile Ser Ser Thr Gln Ala
                85                  90                  95

Pro Pro Glu Thr Thr Thr Thr Glu Arg Pro Pro Lys Gln Ile Pro Pro
            100                 105                 110

Asn Leu His Glu Val Cys Gly Ile His Asn Thr Thr Thr Thr Arg Ile
        115                 120                 125

Ile Gly Gly Arg Glu Ala Pro Ile Gly Ala Trp Pro Trp Met Thr Ala
    130                 135                 140

Val Tyr Ile Lys Gln Gly Gly Ile Arg Ser Val Gln Cys Gly Gly Ala
145                 150                 155                 160

Leu Val Thr Asn Arg His Val Ile Thr Ala Ser His Cys Val Val Asn
                165                 170                 175
```

```
Ser Ala Gly Thr Asp Val Met Pro Ala Asp Val Phe Ser Val Arg Leu
            180                 185                 190

Gly Glu His Asn Leu Tyr Ser Thr Asp Asp Asp Ser Asn Pro Ile Asp
        195                 200                 205

Phe Ala Val Thr Ser Val Lys His His Glu His Phe Val Leu Ala Thr
    210                 215                 220

Tyr Leu Asn Asp Ile Ala Ile Leu Thr Leu Asn Asp Thr Val Thr Phe
225                 230                 235                 240

Thr Asp Arg Ile Arg Pro Ile Cys Leu Pro Tyr Arg Lys Leu Arg Tyr
                245                 250                 255

Asp Asp Leu Ala Met Arg Lys Pro Phe Ile Thr Gly Trp Gly Thr Thr
            260                 265                 270

Ala Phe Asn Gly Pro Ser Ser Ala Val Leu Arg Glu Val Gln Leu Pro
        275                 280                 285

Ile Trp Glu His Glu Ala Cys Arg Gln Ala Tyr Glu Lys Asp Leu Asn
    290                 295                 300

Ile Thr Asn Val Tyr Met Cys Ala Gly Phe Ala Asp Gly Gly Lys Asp
305                 310                 315                 320

Ala Cys Gln Gly Asp Ser Gly Gly Pro Met Met Leu Pro Val Lys Thr
                325                 330                 335

Gly Glu Phe Tyr Leu Ile Gly Ile Val Ser Phe Gly Lys Lys Cys Ala
            340                 345                 350

Leu Pro Gly Phe Pro Gly Val Tyr Thr Lys Val Thr Glu Phe Leu Asp
        355                 360                 365

Trp Ile Ala Glu His Met Val
    370                 375
```

<210> SEQ ID NO 7
<211> LENGTH: 3078
<212> TYPE: DNA
<213> ORGANISM: Tachypleus tridentatus

<400> SEQUENCE: 7

```
atggtcttag cgtcgttttt ggtgtctggt ttagttctag ggatactagc ccaacaaatg     60

cgtccagttc agtccagagg agtagatctg ggcttgtgtg atgaaacgag gttcgagtgt    120

aagtgtggag atccaggcta tgtgttcaac gtccctatga aacaatgcac gtacttctat    180

cgatggaggc cttattgtaa accatgtgat gacctggagg ctaaggacat ttgtccaaag    240

tacaaacgat gtcaagagtg taaggctggt cttgatagtt gtgttacttg tccacctaac    300

aaatatggta cttggtgtag cggtgaatgt caatgtaaga atggaggtat ctgtgaccag    360

aggacaggag cttgtacctg tcgtgacaga tatgaaggag cgcactgtga aattctcaaa    420

ggttgtcctc ttcttccatc ggattctcaa gttcaggaag tcagaaaccc accagataat    480

ccccaaacta ttgactacag ctgttcacca gggttcaagc ttaaaggcgt ggcacgaatt    540

agctgtctcc caaatggaca gtggagtagc tttccaccca aatgtattcg agaatgtgcc    600

aaggtttcat ctccagaaca cgggaaagtg aatgctccta gtggcaatat gatagaaggg    660

gctactttac ggttctcatg tgatagtccc tactacttga ttggtcaaga aacattaacc    720

tgccagggta atggtcagtg gagtggacaa ataccacaat gtaagaagtt ggtcttctgt    780

cctgaccttg atcctgtaaa ccatgctgaa caccaggtta aaattggtgt ggaacaaaaa    840

tatggtcagt ttcctcaagg cactgaagtg acctatacgt gttcgggtaa ctacttcttg    900

atgggtttta acaccttaaa atgtaaccct gatgggtcct ggtcaggatc acagccatcc    960
```

```
tgtgttaaag tggcagacag agaggtcgac tgtgacagta aagctgtaga cttcttggat   1020
gatgttggtg aacctgtcag gatccactgt cctgctggct gttctttgac agctggtact   1080
gtgtggggta cagccatata ccacgaactt tcctcagtgt gtcgtgcagc catccatgct   1140
ggcaagcttc caaactctgg aggggcggtg catgtagtga acaatggccc ctactcggac   1200
tttctgggta gtgacctgaa tgggataaaa tcggaagagt tgaagtctct tgcccgcagt   1260
tttcgatttg attatgtcag ttcatccaca gcaggtagat caggatgtcc tgatggatgg   1320
tttgaggtag aagagaactg tgtgtacgtt acatcaaaac agagagcctg ggaaagagct   1380
caaggtgtgt gtaccaatat ggctgctcgt cttgctgtgc tagacaaaga tctaattccg   1440
agttccttga ctgagactct acgagggaaa gggttaacaa ccacatggat aggattgcac   1500
agactagatg ctgagaagcc ctttgtttgg gagctaatgg atcgtagtaa tgtggttctg   1560
aatgataacc taacattctg ggcctctggc gaacctggaa atgaaactaa ctgtgtatat   1620
ctggacatcc gagatcagct gcagcctgtg tggaaaacca agtcatgttt tcagccctca   1680
agctttgctt gcatgatgga tttgtcagac agaaataaag ccaaatgcga tgaccctgga   1740
ccactggaaa atggacacgc cacacttcat ggacaaagta ttgatgggtt ctatgctggt   1800
tcttctataa ggtacagctg tgaggttctc cactacctca gtggaactga gaccgtaact   1860
tgtacaacaa atggcacatg gagtgctcct aaacctcgat gtatcaaagt catcacctgc   1920
caaaaccctc ctgtaccatc atatggttct gtggaaatca aacccccaag tcggacaaac   1980
tcgatcagtc gtgttgggtc acctttcttg aggttgccac ggttacccct cccattagcc   2040
agagcagcca aacctcctcc aaaacctaga tcctcacaac cctctactgt ggacttggct   2100
tctaaagtta aactacctga aggtcattac cgggtagggt ctcgagccat ttacacgtgc   2160
gagtcgagat actacgaact acttggatct caaggcagaa gatgtgactc taatggaaac   2220
tggagtggtc ggcccgctag ctgtattcca gtttgtggac ggtcagactc tcctcgttct   2280
cctttcatct ggaatgggaa ttctacagaa ataggtcagt ggccgtggca ggcaggaatc   2340
tctcgatggc ttgcagacca caatatgtgg tttctccagt gtggaggatc cctattgaat   2400
gagaaatgga tcgtcactgc tgcccactgt gtcacctact ctgctactgc tgagataatt   2460
gatcccagtc agtttaaaat ctatctgggc aagtactacc gtgatgacag tagagacgat   2520
gactacgtac aagtaagaga ggctctcgag atccacgtaa atcctaacta cgacccccggc  2580
aatctcaact ttgacatagc cctaattcaa ctgaaaactc ctgttacttt gacaacacga   2640
gtccaaccaa tctgtctgcc tactgacatc acaacaagag aacacttgaa ggagggaaca   2700
ttagcagtgg tgacaggttg gggtttgaat gaaaacaaca catattcaga gatgattcaa   2760
caagctgtgc tacctgttgt tgcagcaagc acctgtgaag aggggtacaa ggaagcagac   2820
ttaccactga cagtaacaga gaacatgttc tgtgcaggtt acaagaaggg acgttatgat   2880
gcctgcagtg gggacagtgg aggaccatta gtgtttgctg atgattcccg taccgaaagg   2940
cggtgggtct tggaagggat tgtcagctgg ggcagtccca gtggatgtgg caaggctaac   3000
cagtatgggg gcttcactaa agttaacgtt tttctatcat ggattaggca gttcattcat   3060
catcaccatc accattga                                                 3078
```

<210> SEQ ID NO 8
<211> LENGTH: 1203
<212> TYPE: DNA
<213> ORGANISM: Tachypleus tridentatus

<400> SEQUENCE: 8

```
atgacctgga tctgcgtgat caccctgttc gctctggctt ccgctaccct gggcaacaag     60
gtgtcccgtg tgggtgtcct gttccccaag acccgtaacg acaacgagtg caccgctcgt    120
ggtggtctga agggctcctg caagtccctg atcgactgcc cctccgtgct ggctaccctg    180
aaggactcct tccccgtcgt gtgctcctgg aacggtcgtt tccagcccat cgtgtgctgc    240
cccgacgcta tcgctccccc ccctgtgacc accaccgctg tgaccgtgat ctccaccaag    300
gagcccaagc tgccccgtct gcacatctcc ggttgcggca agcgcaaggt caagatcgac    360
atcaccaccg tgggccgttc cggttccccc atcctgcccc ccatctccac cccccagaac    420
tccactggtg gtcgtggtat catcgctggc ggtgtcgagg ctaagatcgg tgcttggccc    480
tggatggctg ctgtgttcgt gaagaacttc ggtatcggtc gcttccactg cgctggttcc    540
atcatctcca acaagtacat cctgtccgct gctcacgctt tcctcatcgg tggtcgcaag    600
ctgaccccca cccgtctggc tgtgcgtgtg ggtggtcact acatcaagcg tggccaggag    660
taccccgtca aggacgtgat catccacccc cactacgtgg agaaggagaa ctacaacgac    720
atcgccatca tcgagctgaa ggaggagctg aacttcaccg acctggtcaa ccccatctgc    780
ctgcccgacc ccgagactgt gaccgaccct ctgaaggacc gtatcgtgac cgctgctggc    840
tggggcgacc tggacttctc cggtccccgt tcccaggtgc tgcgtgaggt gtccatcccc    900
gtggtgcccg tggacaagtg cgaccaggct tacgagaagc tgaacacccc ctccctgaag    960
aacggtatta ccaacaactt cctctgcgcc ggactcgagg agggtggcaa ggacgcttgc   1020
cagggcgact ccggtggtcc cctgatgctg gtcaacaaca cccgttggat cgtcgtgggt   1080
gtcgtgtcct tcggtcacaa gtgcgctgag gagggttacc ccggcgtcta ctcccgtgtg   1140
gcttcctacc tggactggat cgctaaggtc accaactccc tggaccacgc tgtcaccaac   1200
taa                                                                 1203
```

<210> SEQ ID NO 9
<211> LENGTH: 1128
<212> TYPE: DNA
<213> ORGANISM: Tachypleus tridentatus

<400> SEQUENCE: 9

```
atgctggtca acaacgtgtt ctccctgctg tgcttccccc tgctgatgtc cgtcgtgcgt     60
tgctccaccc tgtcccgtca gcgtcgtcag ttcgtgttcc ccgacgaaga ggagctgtgc    120
tccaaccgtt tcaccgagga gggcacttgc aagaacgtgc tggactgccg tatcctgctg    180
cagaagaacg actacaacct cctgaaggag tccatctgcg gtttcgaggg tatcactccc    240
aaggtctgct gccccaagtc ctcccacgtg atctccagca cccaggctcc ccccgagact    300
accaccaccg agcgtccccc caagcagatc ccccccaacc tccacgaggt ctgcggtatc    360
cacaacacca ccaccacccg tatcatcggt ggtcgcgagg ctcccatcgg tgcttggccc    420
tggatgaccg ctgtgtacat caagcagggt ggtatccgtt ccgtgcagtg cggaggtgct    480
ctggtcacca accgtcacgt gatcaccgct tcccactgcg tggtcaactc cgctggcacc    540
gacgtgatgc ccgctgacgt gttctctgtg cgtctgggcg agcacaacct gtactccacc    600
gacgacgact ccaaccccat cgacttcgct gtgacctccg tgaagcacca cgagcacttc    660
gtgctggcta cctacctgaa cgacatcgct atcctgactc tgaacgacac cgtgaccttc    720
accgaccgta tccgtcccat ctgcctgccc taccgcaagc tgcgttacga cgacctggct    780
atgcgcaagc ccttcatcac cggctggggc accaccgctt tcaacggtcc ctcctccgct    840
```

-continued

```
gtgctgcgtg aggtgcagct gcccatctgg gagcacgagg cttgccgtca ggcttacgag    900

aaggacctga acatcaccaa cgtgtacatg tgcgctggtt tcgctgacgg tggcaaggac    960

gcttgccagg gcgactccgg tggtcccatg atgctgcccg tcaagaccgg cgagttctac   1020

ctgatcggta tcgtgtcctt cggcaagaag tgcgctctgc ccggtttccc cggtgtctac   1080

accaaggtca ccgagttcct cgactggatc gccgagcaca tggtgtaa                1128


<210> SEQ ID NO 10
<211> LENGTH: 30
<212> TYPE: DNA
<213> ORGANISM: Artificial Sequence
<220> FEATURE:
<223> OTHER INFORMATION: primerFC-N-Pst

<400> SEQUENCE: 10

caactgcaga tggtcttagc gtcgtttttg                                      30


<210> SEQ ID NO 11
<211> LENGTH: 33
<212> TYPE: DNA
<213> ORGANISM: Artificial Sequence
<220> FEATURE:
<223> OTHER INFORMATION: primerFC-notag-R-Bam

<400> SEQUENCE: 11

caggatcctc aaatgaactg cctaatccat gat                                  33


<210> SEQ ID NO 12
<211> LENGTH: 4
<212> TYPE: PRT
<213> ORGANISM: Artificial Sequence
<220> FEATURE:
<223> OTHER INFORMATION: synthesized peptide

<400> SEQUENCE: 12

Ile Glu Gly Arg
1
```